US012605359B2

(12) United States Patent
Tomoda et al.

(10) Patent No.: US 12,605,359 B2
(45) Date of Patent: Apr. 21, 2026

(54) PROPROTEIN CONVERTASE SUBTILISIN/KEXIN TYPE 9 (PCSK9) INHIBITOR AND PHARMACEUTICAL USE THEREFOR

(71) Applicants: THE KITASATO INSTITUTE, Tokyo (JP); LIPOPROTEIN RESEARCH STOCKHOLM AB, Stockholm (SE)

(72) Inventors: Hiroshi Tomoda, Sagamihara (JP); Tohru Nagamitsu, Sagamihara (JP); Satoshi Omura, Sagamihara (JP); Paolo Parini, Stockholm (SE); Osman Ahmed, Stockholm (SE); Matteo Pedrelli, Stockholm (SE); Camilla Pramfalk, Stockholm (SE); Mats Eriksson, Stockholm (SE)

(73) Assignees: THE KITASATO INSTITUTE, Tokyo (JP); LIPOPROTEIN RESEARCH STOCKHOLM AB, Stockholm (SE)

( * ) Notice: Subject to any disclaimer, the term of this patent is extended or adjusted under 35 U.S.C. 154(b) by 819 days.

(21) Appl. No.: 17/795,812

(22) PCT Filed: Jan. 27, 2021

(86) PCT No.: PCT/JP2021/002709

§ 371 (c)(1),
(2) Date: Jul. 27, 2022

(87) PCT Pub. No.: WO2021/153570

PCT Pub. Date: Aug. 5, 2021

(65) Prior Publication Data

US 2023/0100006 A1 Mar. 30, 2023

(30) Foreign Application Priority Data

Jan. 27, 2020 (JP) ................................ 2020-011068

(51) Int. Cl.
*A61K 31/366* (2006.01)
*A61P 1/16* (2006.01)
*A61P 3/06* (2006.01)

(52) U.S. Cl.
CPC .............. *A61K 31/366* (2013.01); *A61P 1/16* (2018.01); *A61P 3/06* (2018.01)

(58) Field of Classification Search
CPC ............. A61K 31/366; A61P 1/16; A61P 3/06
See application file for complete search history.

(56) References Cited

U.S. PATENT DOCUMENTS

| | | | | |
|---|---|---|---|---|
| 8,519,128 | B2 | 8/2013 | Tomoda et al. | |
| 9,187,492 | B2 | 11/2015 | Tomoda et al. | |
| 2010/0081632 | A1* | 4/2010 | Oksenberg | G01N 33/542 435/7.1 |
| 2011/0184173 | A1 | 7/2011 | Tomoda et al. | |
| 2016/0367537 | A1 | 12/2016 | Rudel | |

FOREIGN PATENT DOCUMENTS

| | | | |
|---|---|---|---|
| JP | 5479110 | B2 | 4/2014 |
| JP | 5554330 | B2 | 7/2014 |
| JP | 5592482 | B2 | 9/2014 |
| WO | 2009081957 | A1 | 7/2009 |
| WO | 2014205109 | A2 | 12/2014 |

OTHER PUBLICATIONS

Lopez et al., 355 J. Pharmacol. Exp. Ther. 159-167 (Nov. 2015) (Year: 2015).*
Accad et al., "Massive xanthomatosis and altered composition of atherosclerotic lesions in hyperlipidemic mice lacking acyl CoA:cholesterol acyltransferase 1", The Journal of Clinical Investigation, Mar. 2000, pp. 711-719, vol. 105, No. 6.
Buhman et al., "Resistance to diet-induced hypercholesterolemia and gallstone formation in ACAT2-deficient mice", Nature Medicine, Dec. 2000, pp. 1341-1347, vol. 6, No. 12, Nature America Inc.
Chang et al., "Human Acyl-CoA:cholesterol Acyltransferase (ACAT) and its Potential as a Target for Pharmaceutical Intervention against Atherosclerosis", Acta Biochimica et Biophysica Sinica, 2006, pp. 151-156, vol. 38, No. 3, Institute of Biochemistry and Cell Biology, SIBS, CAS.
Farese, "The Nine Lives of ACAT Inhibitors", Arterioscler. Thromb Vasc Biol., 2006, pp. 1684-1686, vol. 26, American Heart Association, Inc.
Libby, "The Forgotten Majority", Journal of the American College of Cardiology, 2005, pp. 1225-1228, vol. 46, No. 7, Elsevier Inc.
Meuwese et al., "And then there were acyl coenzyme A:cholesterol acly transferase inhibitors", Current Opinion in Lipidology, 2006, pp. 426-431, vol. 17, Lippincott Williams & Wilkins.

(Continued)

*Primary Examiner* — Timothy R Rozof
(74) *Attorney, Agent, or Firm* — The Webb Law Firm

(57) ABSTRACT

A low-molecular weight compound having an activity of inhibiting the functions of proprotein convertase subtilisin/kexin type 9 (PCSK9), a PCSK9 inhibitor containing a compound represented by formula (I), a pharmaceutically acceptable salt thereof, or a pharmaceutically acceptable solvate thereof, as an active component, and a medicament containing the PCSK9 inhibitor as an active component for use in prevention or treatment of one or more symptoms, diseases, or disorders, related to the functions of PCSK9.

(I)

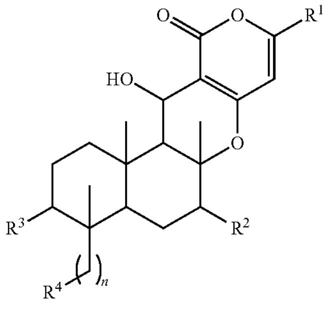

5 Claims, 5 Drawing Sheets

(56) References Cited

OTHER PUBLICATIONS

Nishikido et al., "Non-antibody Approaches to Proprotein Convertase Subtilisin Kexin 9 Inhibition: siRNA, Antisense Oligonucleotides, Adnectins, Vaccination. and New Attempts at Small-Molecule Inhibitors Based on New Discoveries", Frontiers in Cardiovascular Medicine, Jan. 2019, pp. 1-17, vol. 5, Article 199.
Ohshiro et al., "Isoform-specific inhibitors of ACATs: recent advances and promising developments", Future Med. Chem., 2011, pp. 2039-2061, vol. 3, No. 16, Future Science Ltd.
Ohshiro et al., "New Pyripyropene A Derivatives, Highly SOAT2-Selective Inhibitors, Improve Hypercholesterolemia and Atherosclerosis in Atherogenic Mouse Models", The Journal of Pharmacology and Experimental Therapeutics, Nov. 2015, pp. 297-307, vol. 355, The American Society for Pharmacology and Experimental Therapeutics.
Roth, "ACAT Inhibitors: evolution from cholesterol-absorption inhibitors to antiatherosclerotic agents", Drug Discovery Today, Jan. 1998, pp. 19-25, vol. 3, No. 1, Elsevier Science Ltd.
Tomoda et al., "Pyripyropenes, Novel Inhibitors of ACYL-CoA: Cholesterol Acyltransferase Produced by Aspergillus fumigatus", The Journal of Antibiotics, Feb. 1994, pp. 148-153, vol. 47, No. 2, Pfizer Pharmaceuticals Inc.
Xu et al., "Small molecules as inhibitors of PCSK9: Current status and future challenges", European Journal of Medicinal Chemistry, 2019, pp. 212-233, vol. 162, Elsevier Masson SAS.
Yagyu et al., "Absence of ACAT-1 Attentuates Atherosclerosis but Causes Dry Eye and Cutaneous Xanthomatosis in Mice with Congenital Hyperlipidemia", The Journal of Biological Chemistry, Jul. 2000, pp. 21324-21330, vol. 275, No. 28, The American Society for Biochemistry and Molecular Biology, Inc.

* cited by examiner

Fig. 1
Fig. 1A
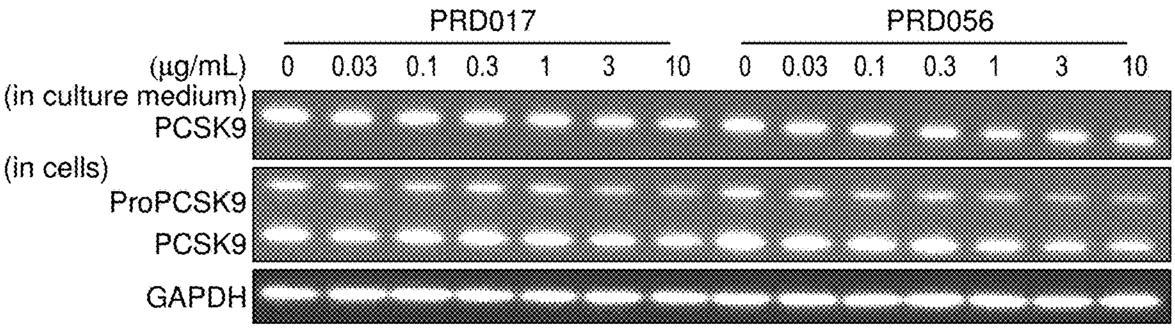
Fig. 1B
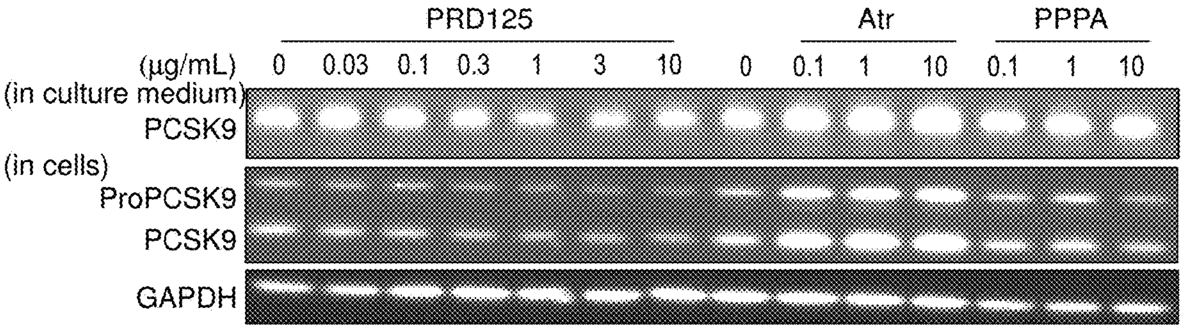

Fig. 3
Fig. 3A
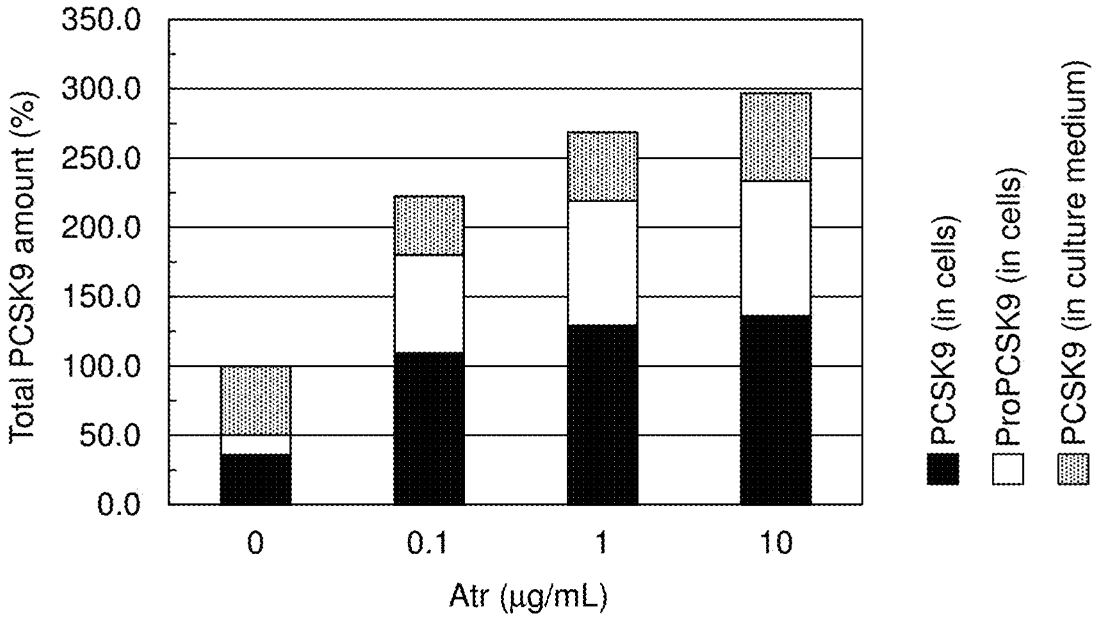
Fig. 3B
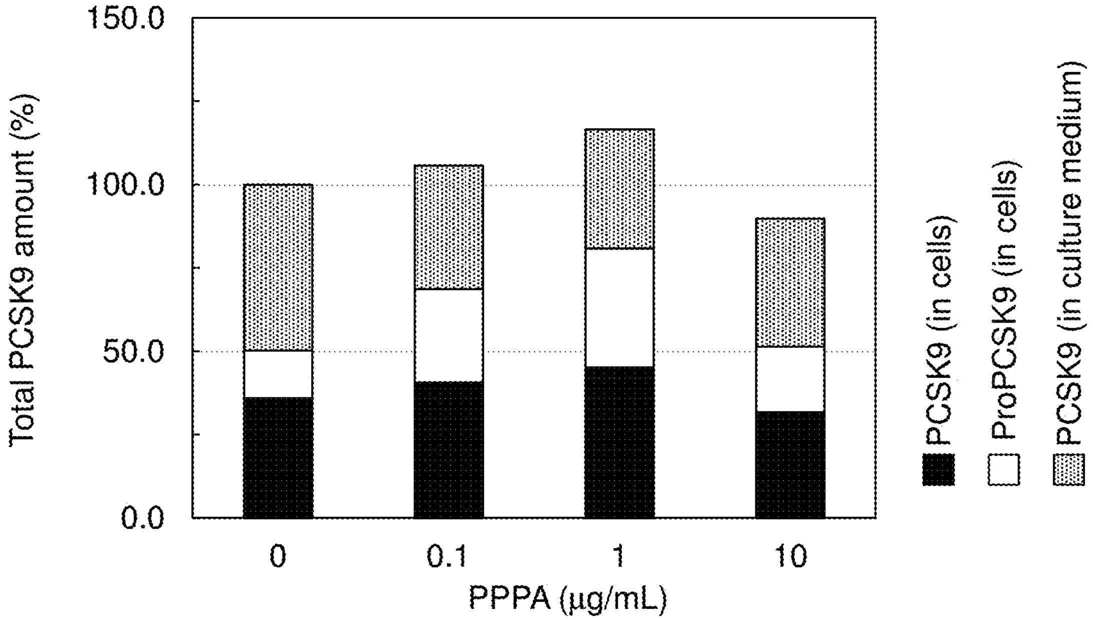

Fig. 4
Fig. 4A
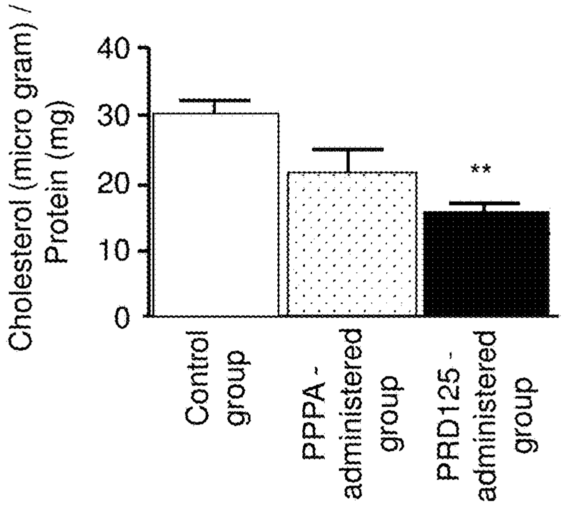
Fig. 4B
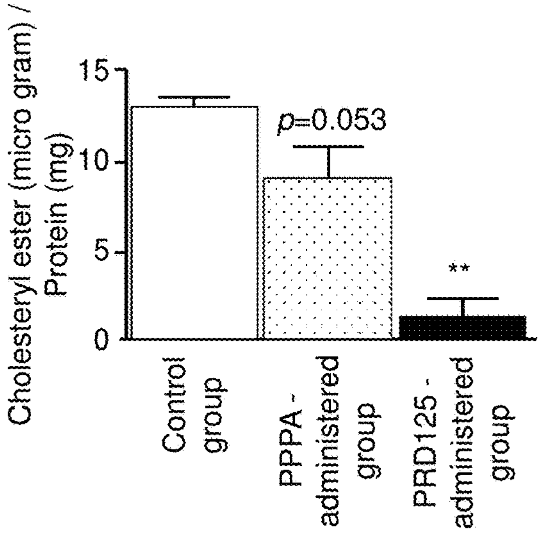
Fig. 4C
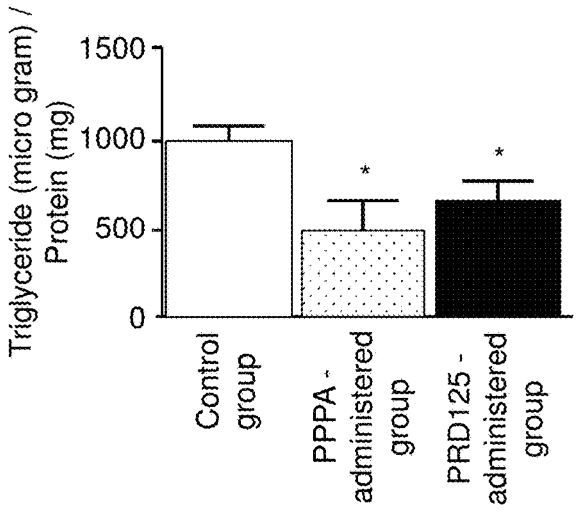
Fig. 4D
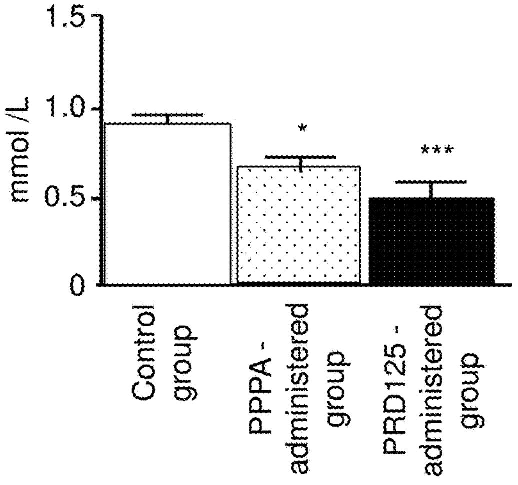

Fig. 5
Fig. 5A
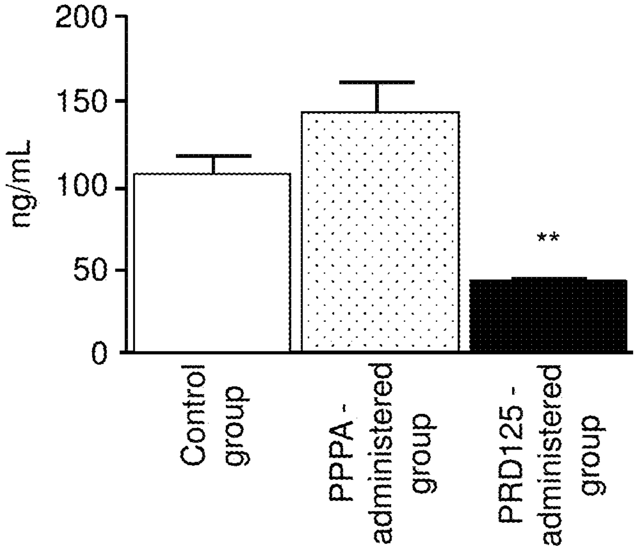
Fig. 5B
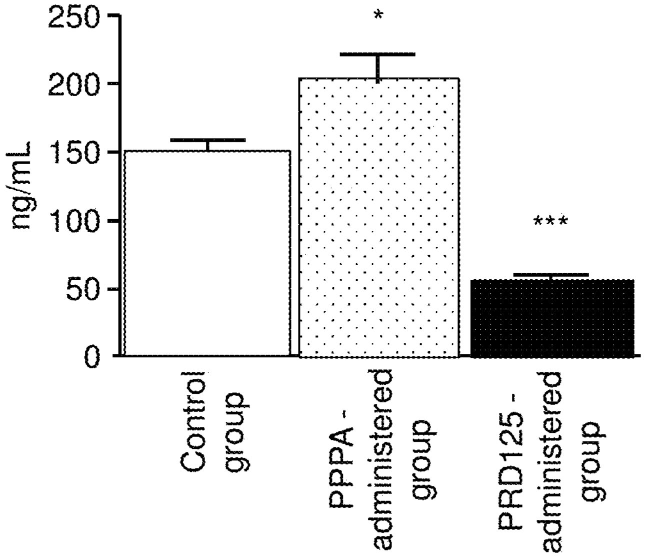

PROPROTEIN CONVERTASE SUBTILISIN/KEXIN TYPE 9 (PCSK9) INHIBITOR AND PHARMACEUTICAL USE THEREFOR

CROSS-REFERENCE TO RELATED APPLICATIONS

This application is the United States national phase of International Application No. PCT/JP2021/002709 filed Jan. 27, 2021, and claims priority to Japanese Patent Application No. 2020-011068 filed Jan. 27, 2020, the disclosures of which are hereby incorporated by reference in their entirety.

BACKGROUND

Technical Field

The present disclosure relates to a proprotein convertase subtilisin/kexin type 9 (which may be hereinafter referred to also as "PCSK9") inhibitor and a pharmaceutical use therefor. In particular, the present disclosure relates to a PCSK9 inhibitor comprising a pyripyropene derivative as an active component and a pharmaceutical use therefor.

Description of Related Art

It is said that the number of patients with arteriosclerosis and dyslipidemia (e.g., hypercholesterolemia and hyperlipidemia) in Japan, who are at high risk of developing death-related diseases such as myocardial infarction or stroke, reaches 30 million, including the pre-disease state without subjective symptoms. In Japan, even at the present time that the guidelines for arteriosclerosis have been revised, deaths that have caused by following the course of the progression of such diseases are still the leading causes of death. Arteriosclerosis and dyslipidemia have become serious health problems not only in Japan but also in Western countries.

Currently, statin drugs that specifically inhibit hydroxy methylglutaryl coenzyme A (hydroxy-3-methylglutaryl Co-A) (which may also be hereinafter referred to as "HMG-CoA") reductase are mainly used as preventive and therapeutic drugs for arteriosclerosis and/or dyslipidemia. Statin drugs have been the best-selling drugs in the world for eight consecutive years from 2001 and are so widely used that two products of the statin drugs are listed in the top 30 sales in 2008.

However, it has become clear that, practically, treatment with statin drugs can only exhibit the onset-suppressing effect on 30 to 40% of the patients receiving treatment and can suppress cardiovascular diseases or the like only in the half of the patients receiving treatment (Libby et al., J. Am. Coll. Cardiol., Vol. 46, Pages 1225-1228, 2005). The reason why HMG-CoA reductase inhibitors like statin drugs that are preventive and therapeutic drugs for arteriosclerosis do not sufficiently suppress cardiovascular diseases or the like is probably because the onset mechanism of arteriosclerosis is complicated. It is considered that arteriosclerosis develops in association with various factors such as genetic factors, medical history such as diabetes, or drug administration history. Therefore, prevention or treatment of arteriosclerosis and/or dyslipidemia requires diagnosis and treatment tailored to the pathological condition of each individual patient. Further, there is an urgent need to develop a drug having a new mechanism of action that is different from the mechanism of action of statin drugs and can be expected to suppress the onset of coronary arteries and/or regress coronary artery lesions.

Sterol O-acyltransferase (which may be hereinafter referred to also as "SOAT") can be listed as examples of the drug target of such a preventive or therapeutic drug for arteriosclerosis and/or dyslipidemia having a new mechanism of action. SOAT refers to the same enzyme as the enzyme conventionally called as cholesterol acyltransferase (which may be hereinafter referred to also as "ACAT") (Roth, Drug Discovery Today, Vol. 3, Pages 19-25, 1998). SOAT is an enzyme that introduces acyl groups into cholesterol. So far, many synthetic SOAT (or ACAT) inhibitors have been developed. However, they have not yet been put to practical clinical use due to problems such as the existence of side effects and insufficient effects (Meuwese et al., Curr. Opin. Lipidol., Vol. 17, Pages 426-431, 2006).

It is known that there are two different types of isozymes, i.e., SOAT1 and SOAT2, which have different functions and localization in the body (Chang et al., Acta. Biochim. Biophys. Sin., Vol. 38, Pages 151-156, 2006). SOAT1 is widely localized in many cells or tissues in vivo and is particularly highly expressed in macrophages or smooth muscle cells. SOAT1 is also known to induce macrophage foaming in the arterial walls, that is the cause of arteriosclerosis. In contrast, SOAT2 is specifically expressed in the small intestine or liver, where SOAT2 is considered to be involved in the absorption of dietary cholesterol and the secretion of very low-density lipoprotein in the respective tissues. In addition, SOAT2 knockout mice showed an anti-arteriosclerosis effect (Buhman et al., Nat. Med., Vol. 6, Pages 1341-1347, 2000). Therefore, it is strongly expected to develop a drug from selective inhibitors to SOAT2, which are isozymes of SOAT for preventing and treating arteriosclerosis and/or dyslipidemia (including hyperlipidemia, fatty liver, and obesity, etc.) (Ohshiro & Tomoda, Future Med. Chem., Vol. 3, Pages 2039-2061, 2011).

As selective inhibitors of SOAT2, pyripyropene A that is a natural organic compound (Tomoda et al., J. Antibiot., Vol. 47, Pages 148-153, 1994) and a pyripyropene derivative group (Japanese Patent No. 5479110, Japanese Patent No. 5554330, and Japanese Patent No. 5592482) obtained by semi-synthetic methods from pyripyropene A have been found.

A proprotein convertase, subtilisin/kexin type 9 (which may be hereinafter referred to also as "PCSK9") can be listed as examples of the drug target of a preventive and therapeutic drug for arteriosclerosis and/or dyslipidemia having another mechanism of action. PCSK9 is a protein that forms a complex with a low-density lipoprotein (which may also be hereinafter referred to as "LDL") receptor and promotes degradation of LDL receptor. PCSK9 is synthesized as a proprotein mainly in the endoplasmic reticulum of the hepatocytes. This proprotein is autocatalytically cleaved, converted to functional (cleaved) PCSK9, and secreted into the blood. The extracellular PCSK9 secreted into the blood binds to LDL receptors on the surface of hepatocytes to form a complex. The complex formed is uptaken into hepatocytes and transported to lysosomes. In the lysosomes, the degradation of LDL receptors is promoted, resulting in an increase in the amount of blood LDL cholesterol level (Nishikido and Ray, Frontiers in Cardiovascular Medicine, Vol. 199, Pages 1-17, 2019).

Based on such a mechanism of action, it was expected to reduce blood cholesterol levels by suppressing the degradation of LDL receptors and promoting the uptake of blood LDL cholesterol into hepatocytes through inhibiting the functions of PCSK9. As therapeutic drugs for familial hypersterolemia or hypercholesterolemia based on such a mechanism of action, antibody drugs such as evolocumab and alirocumab have been commercially launched in Japan. A low-molecular weight compound that can inhibit the functions of PCSK9 has been also developed (Xu et al., European Journal of Medicinal Chemistry, Vol. 162, Pages 212-233, 2019). Further aspects of the existing art are described in: Farese, Arterioscler. Thromb. Vasc. Biol., Vol. 26, Pages 1684-1686, 2006; Yagyu et al., J. Biol. Chem., Vol. 275, Pages 21324-21330, 2000; and Mccad et al., J. Clin. Invest., Vol. 105, Pages 711-719, 2000.

As described above, development of drugs that can inhibit the functions of PCSK9 as preventive or therapeutic drugs for arteriosclerosis and dyslipidemia (e.g., hypercholesterolemia and hyperlipidemia) is in progress based on the mechanism of action that is different from that of statin compounds. However, at present, only drugs marketed in Japan with the approval from the regulatory authorities are antibody drugs such as evolocumab and alirocumab. Although antibody drugs can be expected to be highly effective, they have the problem of high production costs.

Therefore, it is an object of the present disclosure to provide a low-molecular weight compound having an inhibitory activity on the functions of PCSK9.

SUMMARY

The present inventors have examined various means for solving the aforementioned problems. The inventors have found that a specific pyripyropene derivative having an inhibitory activity highly selective to SOAT2 has an inhibitory activity on the functions of PCSK9. The inventors have accomplished the present disclosure based on the finding.

That is, the present disclosure includes the following aspects and embodiments.

(1) A proprotein convertase subtilisin/kexin type 9 (PCSK9) inhibitor comprising a compound represented by formula (I), a pharmaceutically acceptable salt thereof, or a pharmaceutically acceptable solvate thereof, as an active component:

[Formula 1]

(I)

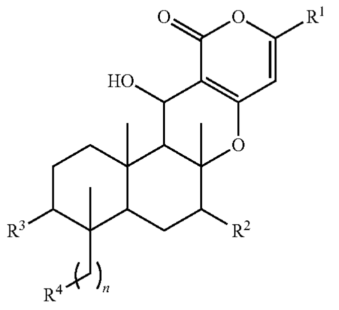

[wherein:

$R^1$ is a substituted or unsubstituted cycloalkyl, a substituted or unsubstituted heterocycloalkyl, a substituted or unsubstituted aryl, or a substituted or unsubstituted heteroaryl;

$R^2$ is hydrogen, a halogen (fluorine, chlorine, bromine, or iodine), cyano, nitro, hydroxyl, a substituted or unsubstituted alkyl, a substituted or unsubstituted alkenyl, a substituted or unsubstituted alkynyl, a substituted or unsubstituted cycloalkyl, a substituted or unsubstituted cycloalkenyl, a substituted or unsubstituted cycloalkynyl, a substituted or unsubstituted heterocycloalkyl, a substituted or unsubstituted cycloalkylalkyl, a substituted or unsubstituted heterocycloalkylalkyl, a substituted or unsubstituted aryl, a substituted or unsubstituted arylalkyl, a substituted or unsubstituted heteroaryl, a substituted or unsubstituted heteroarylalkyl, a substituted or unsubstituted alkoxy, a substituted or unsubstituted cycloalkoxy, a substituted or unsubstituted heterocycloalkoxy, a substituted or unsubstituted aryloxy, a substituted or unsubstituted arylalkyloxy, a substituted or unsubstituted arylalkenyloxy, a substituted or unsubstituted heteroaryloxy, a substituted or unsubstituted heteroarylalkyloxy, a substituted or unsubstituted alkoxycarbonyl, a substituted or unsubstituted cycloalkoxycarbonyl, a substituted or unsubstituted acyl, a substituted or unsubstituted alkylcarbonyloxy, a substituted or unsubstituted arylcarbonyloxy, a substituted or unsubstituted carbamoyl, a substituted or unsubstituted alkylsulfonyl, a substituted or unsubstituted arylsulfonyl, a substituted or unsubstituted alkylsulfanyl, a substituted or unsubstituted arylsulfanyl, or a substituted or unsubstituted amino;

n is 0 or 1;

$R^3$ and $R^4$ are each independently hydrogen, a halogen (fluorine, chlorine, bromine, or iodine), cyano, nitro, hydroxyl, a substituted or unsubstituted alkyl, a substituted or unsubstituted alkenyl, a substituted or unsubstituted alkynyl, a substituted or unsubstituted cycloalkyl, a substituted or unsubstituted cycloalkenyl, a substituted or unsubstituted cycloalkynyl, a substituted or unsubstituted heterocycloalkyl, a substituted or unsubstituted cycloalkylalkyl, a substituted or unsubstituted heterocycloalkylalkyl, a substituted or unsubstituted aryl, a substituted or unsubstituted arylalkyl, a substituted or unsubstituted heteroaryl, a substituted or unsubstituted heteroarylalkyl, a substituted or unsubstituted alkoxy, a substituted or unsubstituted cycloalkoxy, a substituted or unsubstituted heterocycloalkoxy, a substituted or unsubstituted aryloxy, a substituted or unsubstituted arylalkyloxy, a substituted or unsubstituted arylalkenyloxy, a substituted or unsubstituted heteroaryloxy, a substituted or unsubstituted heteroarylalkyloxy, a substituted or unsubstituted alkoxycarbonyl, a substituted or unsubstituted cycloalkoxycarbonyl, a substituted or unsubstituted acyl, a substituted or unsubstituted alkylcarbonyloxy, a substituted or unsubstituted arylcarbonyloxy, a substituted or unsubstituted carbamoyl, a substituted or unsubstituted alkylsulfonyl, a substituted or unsubstituted arylsulfonyl, a substituted or unsubstituted alkylsulfanyl, a substituted or unsubstituted arylsulfanyl, or a substituted or unsubstituted amino, or $R^3$ and $R^4$ together form —O—$CR^5R^6$—O—, wherein:

$R^5$ and $R^6$ are each independently hydrogen, a halogen (fluorine, chlorine, bromine, or iodine), cyano, nitro, hydroxyl, a substituted or unsubstituted alkyl, a substituted or unsubstituted alkenyl, a substituted or unsubstituted alkynyl, a substituted or unsubstituted cycloalkyl, a substituted or unsubstituted cycloalkenyl, a substituted or unsubstituted cycloalkynyl, a substituted or unsubstituted heterocycloalkyl, a substituted or unsubstituted cycloalkylalkyl, a substituted or unsubstituted heterocycloalkylalkyl, a substituted or unsubstituted aryl, a substituted or unsubstituted arylalkyl, a substituted or unsubstituted heteroaryl, a substituted or unsubstituted heteroarylalkyl, a substituted or unsubstituted alkoxy, a substituted or unsubstituted cycloalkoxy, a substituted or unsubstituted heterocycloalkoxy, a substituted or unsubstituted aryloxy, a substituted or unsubstituted arylalkyloxy, a substituted or unsubstituted arylalkenyloxy, a substituted or unsubstituted heteroaryloxy, a substituted or unsubstituted heteroarylalkyloxy, a substituted or unsubstituted alkoxycarbonyl, a substituted or unsubstituted cycloalkoxycarbonyl, a substituted or unsubstituted acyl, a substituted or unsubstituted alkylcarbonyloxy, a substituted or unsubstituted arylcarbonyloxy, a substituted or unsubstituted carbamoyl, a substituted or unsubstituted alkylsulfonyl, a substituted or unsubstituted arylsulfonyl, a substituted or unsubstituted alkylsulfanyl, a substituted or unsubstituted arylsulfanyl, or a substituted or unsubstituted amino;

provided that the case where n is 1, and $R^2$, $R^3$, and $R^4$ are each acetoxy is excepted].

(2) The PCSK9 inhibitor according to embodiment (1) above, wherein:

$R^2$ is hydrogen, hydroxyl, a substituted or unsubstituted $C_1$-$C_6$ alkoxy, a substituted or unsubstituted $C_1$-$C_6$ alkylcarbonyloxy, or a substituted or unsubstituted $C_6$-$C_{18}$ arylcarbonyloxy;

n is 1;

$R^3$ and $R^4$ are each independently hydrogen, hydroxyl, a substituted or unsubstituted $C_1$-$C_6$ alkoxy, a substituted or unsubstituted $C_1$-$C_6$ alkylcarbonyloxy, or a substituted or unsubstituted $C_6$-$C_{18}$ arylcarbonyloxy, or $R^3$ and $R^4$ together form —O—$CR^5R^6$—O—, wherein:

$R^5$ and $R^6$ are each independently hydrogen, a substituted or unsubstituted $C_1$-$C_6$ alkyl, a substituted or unsubstituted $C_2$-$C_6$ alkenyl, a substituted or unsubstituted $C_2$-$C_6$ alkynyl, a substituted or unsubstituted $C_3$-$C_6$ cycloalkyl, a substituted or unsubstituted $C_3$-$C_6$ cycloalkenyl, a substituted or unsubstituted $C_3$-$C_6$ cycloalkynyl, a substituted or unsubstituted 3 to 6-membered heterocycloalkyl, a substituted or unsubstituted $C_6$-$C_{18}$ aryl, a substituted or unsubstituted $C_7$-$C_{20}$ arylalkyl, a substituted or unsubstituted 5 to 15-membered heteroaryl, or a substituted or unsubstituted 5 to 15-membered heteroaryl-$C_1$-$C_6$ alkyl.

(3) The PCSK9 inhibitor according to embodiment (1) or (2) above, wherein:

$R^1$ is a substituted or unsubstituted 5 to 15-membered heteroaryl;

$R^2$ is a substituted or unsubstituted $C_1$-$C_6$ alkylcarbonyloxy, or a substituted or unsubstituted $C_6$-$C_{18}$ arylcarbonyloxy;

n is 1;

$R^3$ and $R^4$ are each independently a substituted or unsubstituted $C_1$-$C_6$ alkylcarbonyloxy, or a substituted or unsubstituted $C_6$-$C_{18}$ arylcarbonyloxy, or $R^3$ and $R^4$ together form —O—$CR^5R^6$—O—, wherein:

$R^5$ and $R^6$ are each independently hydrogen, or a substituted or unsubstituted $C_6$-$C_{18}$ aryl.

(4) The PCSK9 inhibitor according to any one of embodiments (1) to (3) above, wherein:

$R^1$ is pyridine-3-yl;

$R^2$ is acetoxy or 4-cyanobenzoyloxy;

n is 1;

both of $R^3$ and $R^4$ are acetoxy, or $R^3$ and $R^4$ together form —O—$CR^5R^6$—O—; wherein:

$R^5$ is hydrogen; and $R^6$ is 2-methylphenyl.

(5) A medicament comprising the PCSK9 inhibitor according to any one of embodiments (1) to (4) above as an active component for use in prevention or treatment of one or more symptoms, diseases, or disorders, related to the functions of PCSK9, selected from the group consisting of hypercholesterolemia, familial hypersterolemia, hyperlipidemia, arteriosclerosis, fatty liver, adiposity, pancreatic beta cell failure, cholesteryl ester accumulation, Wolman's disease, Niemann Pick's disease type C, symptoms in the survivors of Hodgkin's lymphangioma, Tangier disease, Kawasaki's disease, sitosterolemia, juvenile idiopathic arthritis, familial hypercholesterolemia, diabetes, symptoms in kidney transplant patients, and symptoms in heart transplant patients.

(6) The medicament according to embodiment (5) above, wherein the fatty liver is non-alcoholic steatohepatitis (NASH) or non-alcoholic fatty liver disease (NAFLD).

(7) The medicament according to embodiment (5) above, wherein the arteriosclerosis is atherosclerosis.

(8) A pharmaceutical composition comprising the PCSK9 inhibitor according to any one of embodiments (1) to (4) above, or the compound defined in any one of embodiments (1) to (4) above, the pharmaceutically acceptable salt thereof, or the pharmaceutically acceptable solvate thereof, and one or more pharmaceutically acceptable carriers, for use in prevention or treatment of one or more symptoms, diseases, or disorders, related to the functions of PCSK9, selected from the group consisting of hypercholesterolemia, familial hypersterolemia, hyperlipidemia, arteriosclerosis, fatty liver, adiposity, pancreatic beta cell failure, cholesteryl ester accumulation, Wolman's disease, Niemann Pick's disease type C, symptoms in the survivors of Hodgkin's lymphangioma, Tangier disease, Kawasaki's disease, sitosterolemia, juvenile idiopathic arthritis, familial hypercholesterolemia, diabetes, symptoms in kidney transplant patients, and symptoms in heart transplant patients.

(9) A pharmaceutical composition according to embodiment (8) above, wherein the fatty liver is non-alcoholic steatohepatitis (NASH) or non-alcoholic fatty liver disease (NAFLD).

(10) A pharmaceutical composition according to embodiment (8) above, wherein the arteriosclerosis is atherosclerosis.

(11) A method for preventing or treating the symptoms, diseases, and/or disorders, the method comprising administering an effective amount of the PCSK9 inhibitor according to any one of embodiments (1) to (4) above, or the compound defined in any one of embodiments (1) to (4) above, the pharmaceutically acceptable salt thereof, or the pharmaceutically acceptable solvate thereof, to a subject in need of prevention or treatment of one or more symptoms, diseases, or disorders, related to the functions of PCSK9, selected from the group consisting of hypercholesterolemia, familial hypersterolemia, hyperlipidemia, arteriosclerosis, fatty liver, adiposity, pancreatic beta cell failure, cholesteryl ester accumulation, Wolman's disease, Niemann Pick's disease type C, symptoms in the survivors of Hodgkin's lymphangioma, Tangier disease, Kawasaki's disease, sitosterolemia, juvenile idiopathic arthritis, familial hypercholesterolemia, diabetes, symptoms in kidney transplant patients, and symptoms in heart transplant patients.

(12) The method according to embodiment (11) above, wherein the fatty liver is non-alcoholic steatohepatitis (NASH) or non-alcoholic fatty liver disease (NAFLD).

(13) The method according to embodiment (11) above, wherein the arteriosclerosis is atherosclerosis.

(14) The PCSK9 inhibitor according to any one of embodiments (1) to (4) above, or the compound defined in any one of embodiments (1) to (4) above, the pharmaceutically acceptable salt thereof, or the pharmaceutically acceptable solvate thereof, for use in prevention or treatment of one or more symptoms, diseases, or disorders, related to the functions of PCSK9, selected from the group consisting of hypercholesterolemia, familial hypersterolemia, hyperlipidemia, arteriosclerosis, fatty liver, adiposity, pancreatic beta cell failure, cholesteryl ester accumulation, Wolman's disease, Niemann Pick's disease type C, symptoms in the survivors of Hodgkin's lymphangioma, Tangier disease, Kawasaki's disease, sitosterolemia, juvenile idiopathic arthritis, familial hypercholesterolemia, diabetes, symptoms in kidney transplant patients, and symptoms in heart transplant patients.

(15) A PCSK9 inhibitor, or a compound or a pharmaceutically acceptable salt thereof, or a pharmaceutically acceptable solvate thereof for the use according to embodiment (14) above, wherein the fatty liver is non-alcoholic steatohepatitis (NASH) or non-alcoholic fatty liver disease (NAFLD).

(16) A PCSK9 inhibitor, or a compound, a pharmaceutically acceptable salt thereof, or a pharmaceutically acceptable solvate thereof for the use according to embodiment (14) above, wherein the arteriosclerosis is atherosclerosis.

(17) Use of the PCSK9 inhibitor according to any one of embodiments (1) to (4) above, or the compound defined in any one of embodiments (1) to (4) above, the pharmaceutically acceptable salt thereof, or the pharmaceutically acceptable solvate thereof, in production of a medicament for prevention or treatment of one or more symptoms, diseases, or disorders, related to the functions of PCSK9, selected from the group consisting of hypercholesterolemia, familial hypersterolemia, hyperlipidemia, arteriosclerosis, fatty liver, adiposity, pancreatic beta cell failure, cholesteryl ester accumulation, Wolman's disease, Niemann Pick's disease type C, symptoms in the survivors of Hodgkin's lymphangioma, Tangier disease, Kawasaki's disease, sitosterolemia, juvenile idiopathic arthritis, familial hypercholesterolemia, diabetes, symptoms in kidney transplant patients, and symptoms in heart transplant patients.

(18) Use of the PCSK9 inhibitor according to any one of embodiments (1) to (4) above, or the compound defined in any one of embodiments (1) to (4) above, the pharmaceutically acceptable salt thereof, or the pharmaceutically acceptable solvate thereof, for prevention or treatment of one or more symptoms, diseases, or disorders, related to the functions of PCSK9, selected from the group consisting of hypercholesterolemia, familial hypersterolemia, hyperlipidemia, arteriosclerosis, fatty liver, adiposity, pancreatic beta cell failure, cholesteryl ester accumulation, Wolman's disease, Niemann Pick's disease type C, symptoms in the survivors of Hodgkin's lymphangioma, Tangier disease, Kawasaki's disease, sitosterolemia, juvenile idiopathic arthritis, familial hypercholesterolemia, diabetes, symptoms in kidney transplant patients, and symptoms in heart transplant patients.

(19) The use according to embodiment (17) or (18) above, wherein the fatty liver is non-alcoholic steatohepatitis (NASH) or non-alcoholic fatty liver disease (NAFLD).

(20) The use according to embodiment (17) or (18) above, wherein the arteriosclerosis is atherosclerosis.

One aspect of the present disclosure can provide a low-molecular weight compound having an activity of inhibiting the functions of PCSK9.

Problems, configurations, and effects other than the above will be clarified by the following description of the embodiments.

This description includes the contents described in the description and/or drawings of Japanese Patent Application No. 2020-011068, which is the basis of the priority of the present application.

BRIEF DESCRIPTION OF THE DRAWINGS

FIG. 1 shows images indicating the results of detecting PCSK9 and ProPCSK9 in the culture medium and the cells in test I-1 by Western blotting, wherein FIG. 1A indicates the results of detecting PCSK9 and ProPCSK9 in the culture medium and the cells with PRD017 or PRD056 added, and FIG. 1B indicates the results of detecting PCSK9 and ProPCSK9 in the culture medium and the cells with PRD125, atorvastatin (Atr), or pyripyropene A (PPPA) added;

FIG. 3 shows graphs indicating the results of quantifying the band intensity of PCSK9 detected by Western blotting in test I-1, wherein FIG. 3A indicates the results with Atr added, and FIG. 3B indicates the results with PPPA added, respectively, wherein the horizontal axis indicates the concentration of the compound (micro gram/mL) added, and the vertical axis indicates the total amount of PCSK9(%), respectively;

FIG. 4 shows graphs indicating the amount of neutral lipids in the liver and blood in test 1-2, wherein FIG. 4A indicates the amount of total cholesterol in the liver, FIG. 4B indicates the amount of cholesteryl ester in the liver, FIG. 4C indicates the amount of triglyceride in the liver, and FIG. 4D indicates the amount of LDL-cholesterol in the blood, respectively; and FIG. 5 shows graphs indicating the amount of PCSK9 in the blood in test 1-2, wherein FIG. 5A indicates the amount of PCSK9 in the blood of male mice, and FIG. 5B indicates the amount of PCSK9 in the blood of female mice, respectively.

DETAILED DESCRIPTION

Figures 2, 2A:
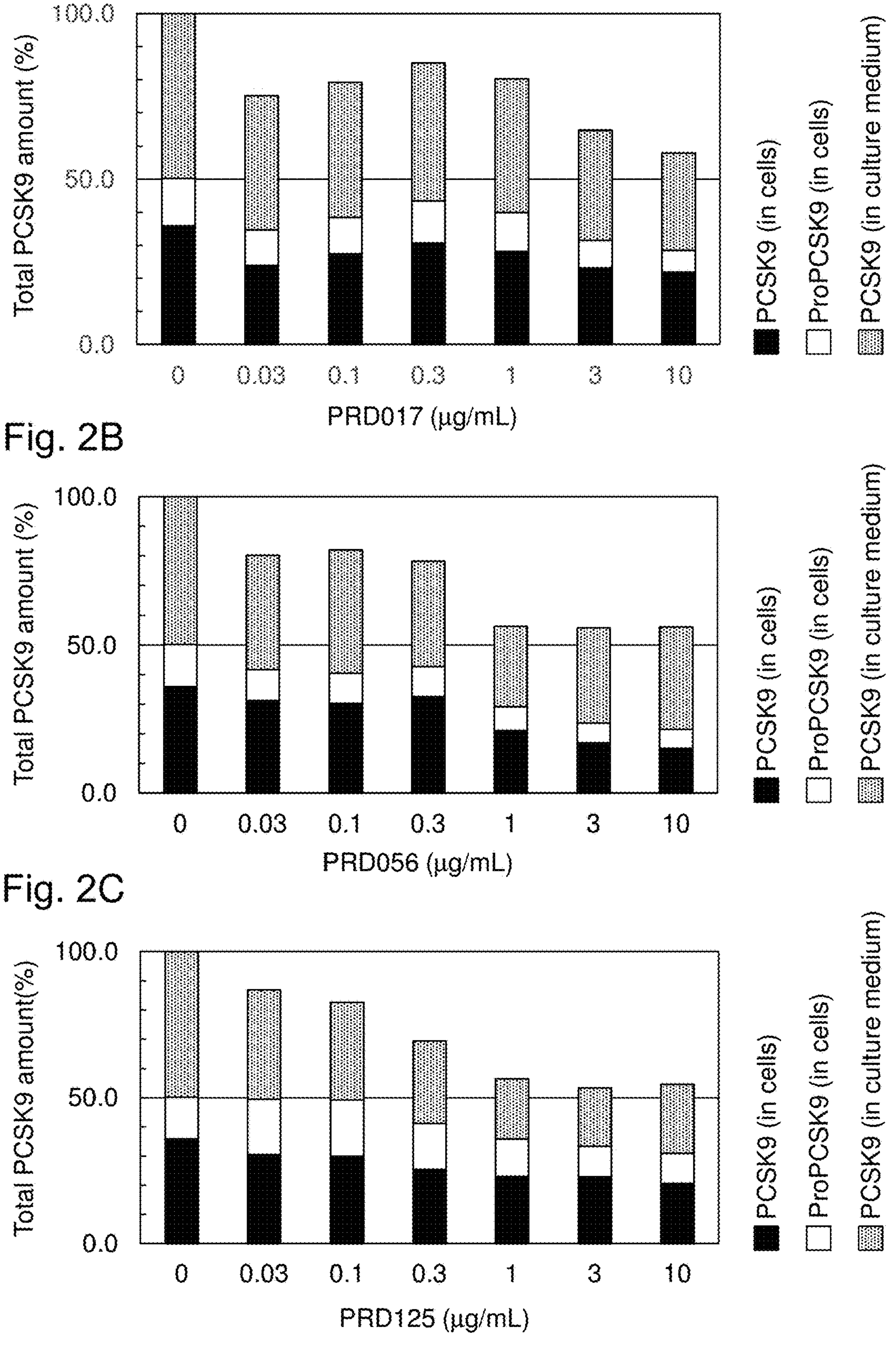
FIG. 2 shows graphs indicating the results of quantifying the band intensity of PCSK9 detected by Western blotting in test I-1, wherein FIG. 2A indicates the results with PRD017 added, FIG. 2B indicates the results with PRD056 added, and FIG. 2C indicates the results with PRD125 added, respectively, and wherein the horizontal axis indicates the concentration of the compound (micro gram/mL) added, and the vertical axis indicates the total amount of PCSK9(%), respectively.

Hereinafter, the preferable embodiments of the present disclosure will be described in detail.

<1. Compound as an Active Component>

In this description, "alkyl" means a linear- or branched-chain structured saturated aliphatic hydrocarbon group containing a specific number of carbon atoms. For example, "$C_1$-$C_6$ alkyl" means a linear- or branched-chain structured saturated aliphatic hydrocarbon group containing at least one and at most six carbon atoms. Suitable examples of the alkyl can include, but not limited to, linear- or branched-chain structured $C_1$-$C_6$ alkyls such as methyl, ethyl, n-propyl, isopropyl, n-butyl, sec-butyl, isobutyl, tert-butyl, n-pentyl, and n-hexyl.

In this description, "alkenyl" means a group in which one or more C—C single bonds of the alkyl are substituted with double bonds. Suitable examples of the alkenyl can include, but not limited to, linear- or branched-chain structured $C_2$-$C_6$ alkenyls such as vinyl, 1-propenyl, allyl, 1-methylethenyl (isopropenyl), 1-butenyl, 2-butenyl, 3-butenyl, 1-methyl-2-propenyl, 2-methyl-2-propenyl, 1-methyl-1-propenyl, 2-methyl-1-propenyl, 1-pentenyl, and 1-hexenyl.

In this description, "alkynyl" means a group in which one or more C—C single bonds of the alkyl are substituted with triple bonds. Suitable examples of the alkynyl can include, but not limited to, linear- or branched-chain structured $C_2$-$C_6$ alkynyls such as ethynyl, 1-propinyl, 2-propinyl, 1-butynyl, 2-butynyl, 3-butynyl, 1-methyl-2-propinyl, 1-pentynyl, and 1-hexynyl.

In this description, "cycloalkyl" means alicyclic alkyl containing a specific number of carbon atoms. For example, "$C_3$-$C_6$ cycloalkyl" means a cyclic hydrocarbon group containing at least three and at most six carbon atoms. Suitable examples of the cycloalkyl can include, but not limited to, $C_3$-$C_6$ cycloalkyls such as cyclopropyl, cyclobutyl, cyclopentyl, and cyclohexyl.

In this description, "cycloalkenyl" means a group in which one or more C—C single bonds of the cycloalkyl are substituted with double bonds. Suitable examples of the cycloalkenyl can include, but not limited to, $C_4$-$C_6$ cycloalkenyls such as cyclobutenyl, cyclopentenyl, and cyclohexenyl.

In this description, "cycloalkynyl" means a group in which one or more C—C single bonds of the cycloalkyl are substituted with triple bonds. Suitable examples of the cycloalkynyl can include, but not limited to, $C_4$-$C_6$ cycloalkynyls such as cyclobutynyl, cyclopentynyl, and cyclohexynyl.

In this description, "heterocycloalkyl" means a group in which one or more carbon atoms of the cycloalkyl, the cycloalkenyl, or the cycloalkynyl each independently are substituted with one or more heteroatoms selected from nitrogen (N), sulfur (S), and oxygen (O). In this case, the substitution with N or S includes substitution with N-oxide or with S-oxide or -dioxide, respectively. Suitable examples of the heterocycloalkyl can include, but not limited to, 3 to 6-membered heterocycloalkyls such as pyrrolidinyl, tetrahydrofuranyl, dihydrofuranyl, tetrahydrothienyl, tetrahydropyranyl, dihydropyranyl, tetrahydrothiopyranyl, piperidinyl, morpholinyl, thiomorpholinyl, and piperazinyl.

In this description, "cycloalkylalkyl" means a group in which one of the hydrogen atoms of the alkyl, the alkenyl, or the alkynyl is substituted with the cycloalkyl, the cycloalkenyl, or the cycloalkynyl. Suitable examples of the cycloalkylalkyl can include, but not limited to, $C_7$-$C_{11}$ cycloalkylalkyls such as cyclohexylmethyl and cyclohexenylmethyl.

In this description, "heterocycloalkylalkyl" means a group in which one of the hydrogen atoms of the alkyl, the alkenyl, or the alkynyl is substituted with the heterocycloalkyl. Suitable examples of the heterocycloalkylalkyl can include, but not limited to, 3 to 6-membered heterocycloalkyl-$C_1$-$C_6$ alkyls.

In this description, "alkoxy" and "alkoxyl" each mean a group in which a hydrogen atom of the hydroxyl is substituted with the alkyl, the alkenyl, or the alkynyl. Suitable examples of the alkoxy and alkoxyl can include, but not limited to, $C_1$-$C_6$ alkoxys or $C_1$-$C_6$ alkoxyls such as methoxy or methoxyl, ethoxy or ethoxyl, propoxy or propoxyl, butoxy or butoxyl, pentoxy or pentoxyl, and hexoxy or hexoxyl.

In this description, "cycloalkoxy" and "cycloalkoxyl" each mean a group in which a hydrogen atom of the hydroxyl is substituted with the cycloalkyl, the cycloalkenyl, or the cycloalkynyl. Suitable examples of the cycloalkoxy and cycloalkoxyl can include, but not limited to, $C_3$-$C_6$ cycloalkoxys or $C_3$-$C_6$ cycloalkoxyls such as cyclopropoxy or cyclopropoxyl, cyclobutoxy or cyclobutoxyl, and cyclopentoxy or cyclopentoxyl.

In this description, "heterocycloalkoxy" and "heterocycloalkoxyl" each mean a group in which a hydrogen atom of the hydroxyl is substituted with the heterocycloalkyl. Suitable examples of the heterocycloalkoxy and heterocycloalkoxyl can include, but not limited to, 3 to 6-membered heterocycloalkoxyl or 3 to 6-membered heterocycloalkoxyls.

In this description, "aryl" means an aromatic ring group. Suitable examples of the aryl can include, but not limited to, $C_6$-$C_{18}$ aryls such as phenyl, biphenyl, terphenyl, naphthyl, and anthracenyl.

In this description, "arylalkyl" means a group in which one of the hydrogen atoms of the alkyl, the alkenyl, or the alkynyl is substituted with the aryl. Suitable examples of the arylalkyl can include, but not limited to, $C_7$-$C_{20}$ arylalkyls such as benzyl, 1-phenethyl, 2-phenethyl, biphenylmethyl, terphenylmethyl, and styryl.

In this description, "heteroaryl" means a group in which one or more carbon atoms of the aryl each independently are substituted with one or more heteroatoms selected from N, S, and O. In this case, the substitution with N or S includes substitution with N-oxide or with S-oxide or -dioxide, respectively. Suitable examples of the heteroaryl can include, but not limited to, 5 to 15-membered heteroaryls such as furanyl, thienyl (thiophenyl), pyrrolyl, imidazolyl, pyrazolyl, triazolyl, tetrazolyl, triazolyl, oxazolyl, isoxazolyl, oxadiazolyl, thiadiazolyl, isothiazolyl, pyridyl, pyridazinyl, pyrazinyl, pyrimidinyl, quinolinyl, isoquinolinyl, and indolyl.

In this description, "heteroarylalkyl" means a group in which one of the hydrogen atoms of the alkyl, the alkenyl, or the alkynyl is substituted with the heteroaryl. Suitable examples of the heteroarylalkyl can include, but not limited to, 5 to 15-membered heteroaryl-$C_1$-$C_6$ alkyls such as pyridylmethyl.

In this description, "aryloxy" means a group in which a hydrogen atom of the hydroxyl is substituted with the aryl. Suitable examples of the aryloxy can include, but not limited to, $C_6$-$C_{18}$ aryloxys such as phenoxy, biphenyloxy, naphthyloxy, and anthryloxy (anthracenyloxy).

In this description, "arylalkyloxy" means a group in which a hydrogen atom of the hydroxyl is substituted with the arylalkyl. Suitable examples of the arylalkyloxy can include, but not limited to, $C_7$-$C_{20}$ arylalkyloxys such as benzyloxy, 1-phenethyloxy, 2-phenethyloxy, and styryloxy.

In this description, "heteroaryloxy" means a group in which a hydrogen atom of the hydroxyl is substituted with the heteroaryl. Suitable examples of the heteroaryloxy can include, but not limited to, 5 to 15-membered heteroaryloxys such as furanyloxy, thienyloxy (thiophenyloxy), pyrrolyloxy, imidazolyloxy, pyrazolyloxy, triazolyloxy, tetrazolyloxy, triazolyloxy, oxazolyloxy, isoxazolyloxy, oxadiazolyloxy, thiadiazolyloxy, isothiazolyloxy, pyridyloxy, pyridazinyloxy, pyrazinyloxy, pyrimidinyloxy, quinolinyloxy, isoquinolinyloxy, and indolyloxy.

In this description, "heteroarylalkyloxy" means a group in which a hydrogen atom of the hydroxyl is substituted with the heteroarylalkyl. Suitable examples of the heteroarylalkyloxy can include, but not limited to, 5 to 15-membered heteroaryl-$C_1$-$C_6$ alkyloxys.

In this description, "acyl" means a group in which a monovalent group selected from the groups described above and a carbonyl are linked. Suitable examples of the acyl can include, but not limited to, $C_1$-$C_{20}$ acyls including $C_1$-$C_6$ aliphatic acyls such as formyl, acetyl, and propionyl and $C_7$-$C_{20}$ aromatic acyls such as benzoyl.

The groups described above can be each independently unsubstituted or further substituted with one or a plurality of monovalent groups described above.

In this description, "halogen" or "halo" means fluorine (F), chlorine (Cl), bromine (Br), or iodine (I).

One aspect of the present disclosure relates to a PCSK9 inhibitor containing a compound represented by formula (I):

[Formula 2]

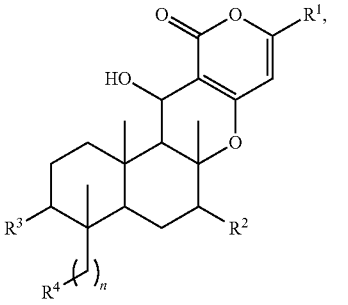

(I)

a pharmaceutically acceptable salt thereof, or a pharmaceutically acceptable solvate thereof, as an active component.

The present inventors have found that a specific pyripyropene derivative having an inhibitory activity highly selective to SOAT2 has an inhibitory activity on the functions of PCSK9. It is known that pyripyropene derivatives have high SOAT2 inhibitory activity and can be used in prevention or treatment of diseases or symptoms such as dyslipidemia, arteriosclerosis, hypertension, fatty liver, and adiposity through the SOAT2 inhibitory activity. However, the fact that a pyripylopen derivative has an inhibitory activity on the function of PCSK9 is a novel finding that has not been known so far. Also, there was no prior art suggesting that a compound having a SOAT2 inhibitory activity, such as a pyripylopen derivative, could be associated with exhibition of the functions of PCSK9.

A pyripyropene derivative can be produced from pyripyropene A by a semi-synthetic method. Further, pyripyropene A can be produced at a relatively low cost by a culture method using a microorganism capable of producing the compound. Therefore, the compound represented by formula (I), which is the active component of the PCSK9 inhibitor of this aspect, can be obtained at a lower production cost as compared with antibody drugs such as evolocumab and alirocumab.

As described below, the compound represented by formula (I), which is the active component of the PCSK9 inhibitor of this aspect, has an inhibitory activity on the functions of PCSK9, whereas atorvastatin, which is a known statin drug for preventing or treating arteriosclerosis and/or dyslipidemia through inhibition of HMG-CoA reductase, does not inhibit, but rather promotes, the functions of PCSK9. Thus, since the compound represented by formula (I), which is the active component of the PCSK9 inhibitor of this aspect, has an activity exhibition pattern different from that of the known statin drug atorvastatin, the compound of the present disclosure can provide a significant preventive or therapeutic effect on a subject who could not have enjoyed sufficient preventive or therapeutic effects by known statin drugs.

In formula (I), $R^1$ is a substituted or unsubstituted cycloalkyl, a substituted or unsubstituted heterocycloalkyl, a substituted or unsubstituted aryl, or a substituted or unsubstituted heteroaryl. $R^1$ is preferably a substituted or unsubstituted $C_3$-$C_6$ cycloalkyl, a substituted or unsubstituted 3 to 6-membered heterocycloalkyl, a substituted or unsubstituted $C_6$-$C_{18}$ aryl, or a substituted or unsubstituted 5 to 15-membered heteroaryl; more preferably a substituted or unsubstituted 5 to 15-membered heteroaryl; particularly preferably pyridine-3-yl.

In formula (I), $R^2$ is hydrogen, a halogen (fluorine, chlorine, bromine, or iodine), cyano, nitro, hydroxyl, a substituted or unsubstituted alkyl, a substituted or unsubstituted alkenyl, a substituted or unsubstituted alkynyl, a substituted or unsubstituted cycloalkyl, a substituted or unsubstituted cycloalkenyl, a substituted or unsubstituted cycloalkynyl, a substituted or unsubstituted heterocycloalkyl, a substituted or unsubstituted cycloalkylalkyl, a substituted or unsubstituted heterocycloalkylalkyl, a substituted or unsubstituted aryl, a substituted or unsubstituted arylalkyl, a substituted or unsubstituted heteroaryl, a substituted or unsubstituted heteroarylalkyl, a substituted or unsubstituted alkoxy, a substituted or unsubstituted cycloalkoxy, a substituted or unsubstituted heterocycloalkoxy, a substituted or unsubstituted aryloxy, a substituted or unsubstituted arylalkyloxy, a substituted or unsubstituted arylalkenyloxy, a substituted or unsubstituted heteroaryloxy, a substituted or unsubstituted heteroarylalkyloxy, a substituted or unsubstituted alkoxycarbonyl, a substituted or unsubstituted cycloalkoxycarbonyl, a substituted or unsubstituted acyl, a substituted or unsubstituted alkylcarbonyloxy, a substituted or unsubstituted arylcarbonyloxy, a substituted or unsubstituted carbamoyl, a substituted or unsubstituted alkylsulfonyl, a substituted or unsubstituted arylsulfonyl, a substituted or unsubstituted alkylsulfanyl, a substituted or unsubstituted arylsulfanyl, or a substituted or unsubstituted amino. $R^2$ is preferably hydrogen, a halogen (fluorine, chlorine, bromine, or iodine), cyano, nitro, hydroxyl, a substituted or unsubstituted $C_1$-$C_6$ alkyl, a substituted or unsubstituted $C_2$-$C_6$ alkenyl, a substituted or unsubstituted $C_2$-$C_6$ alkynyl, a substituted or unsubstituted $C_3$-$C_6$ cycloalkyl, a substituted or unsubstituted $C_3$-$C_6$ cycloalkenyl, a substituted or unsubstituted $C_3$-$C_6$ cycloalkynyl, a substituted or unsubstituted 3 to 6-membered heterocycloalkyl, a substituted or unsubstituted $C_7$-$C_{11}$ cycloalkylalkyl, a substituted or unsubstituted 3 to 6-membered heterocycloalkyl-$C_1$-$C_6$ alkyl, a substituted or unsubstituted $C_6$-$C_{18}$ aryl, a substituted or unsubstituted $C_7$-$C_{20}$ arylalkyl, a substituted or unsubstituted 5 to 15-membered heteroaryl, a substituted or unsubstituted 5 to 15-membered heteroaryl-$C_1$-$C_6$ alkyl, a substituted or unsubstituted $C_1$-$C_6$ alkoxy, a substituted or unsubstituted $C_3$-$C_6$ cycloalkoxy, a substituted or unsubstituted 3 to 6-membered heterocycloalkoxy, a substituted or unsubstituted $C_6$-$C_{18}$ aryloxy, a substituted or unsubstituted $C_7$-$C_{20}$ arylalkyloxy, a substituted or unsubstituted $C_7$-$C_{20}$ arylalkenyloxy, a substituted or unsubstituted 5 to 15-membered heteroaryloxy, a substituted or unsubstituted 5 to 15-membered heteroaryl-$C_1$-$C_6$ alkyloxy, a substituted or unsubstituted $C_1$-$C_6$ alkoxycarbonyl, a substituted or unsubstituted $C_3$-$C_6$ cycloalkoxycarbonyl, a substituted or unsubstituted $C_1$-$C_{20}$ acyl, a substituted or unsubstituted $C_1$-$C_6$ alkylcarbonyloxy, a substituted or unsubstituted $C_6$-$C_{18}$ arylcarbonyloxy, a substituted or unsubstituted carbamoyl, a substituted or unsubstituted $C_1$-$C_6$ alkylsulfonyl, a substituted or unsubstituted $C_6$-$C_{18}$ arylsulfonyl, a substituted or unsubstituted $C_1$-$C_6$ alkylsulfanyl, a substituted or unsubstituted $C_6$-$C_{10}$ arylsulfanyl, or a substituted or unsubstituted amino; more preferably hydrogen, hydroxyl, a substituted or unsubstituted $C_1$-$C_6$ alkoxy, a substituted or unsubstituted $C_1$-$C_6$ alkylcarbonyloxy, or a substituted or unsubstituted $C_6$-$C_{18}$ arylcarbonyloxy; further preferably a substituted or unsubstituted $C_1$-$C_6$ alkylcarbonyloxy, or a substituted or unsubstituted $C_6$-$C_{18}$ arylcarbonyloxy; particularly preferably acetoxy or 4-cyanobenzoyloxy.

In formula (I), n is 0 or 1, preferably, n is 1.

In formula (I), $R^3$ and $R^4$ are each independently hydrogen, a halogen (fluorine, chlorine, bromine, or iodine), cyano, nitro, hydroxyl, a substituted or unsubstituted alkyl, a substituted or unsubstituted alkenyl, a substituted or unsubstituted alkynyl, a substituted or unsubstituted cycloalkyl, a substituted or unsubstituted cycloalkenyl, a substituted or unsubstituted cycloalkynyl, a substituted or unsubstituted heterocycloalkyl, a substituted or unsubstituted cycloalkylalkyl, a substituted or unsubstituted heterocycloalkylalkyl, a substituted or unsubstituted aryl, a substituted or unsubstituted arylalkyl, a substituted or unsubstituted heteroaryl, a substituted or unsubstituted heteroarylalkyl, a substituted or unsubstituted alkoxy, a substituted or unsubstituted cycloalkoxy, a substituted or unsubstituted heterocycloalkoxy, a substituted or unsubstituted aryloxy, a substituted or unsubstituted arylalkyloxy, a substituted or unsubstituted arylalkenyloxy, a substituted or unsubstituted heteroaryloxy, a substituted or unsubstituted heteroarylalkyloxy, a substituted or unsubstituted alkoxycarbonyl, a substituted or unsubstituted cycloalkoxycarbonyl, a substituted or unsubstituted acyl, a substituted or unsubstituted alkylcarbonyloxy, a substituted or unsubstituted arylcarbonyloxy, a substituted or unsubstituted carbamoyl, a substituted or unsubstituted alkylsulfonyl, a substituted or unsubstituted arylsulfonyl, a substituted or unsubstituted alkylsulfanyl, a substituted or unsubstituted arylsulfanyl, or a substituted or unsubstituted amino, or $R^3$ and $R^4$ together form —O—$CR^5R^6$—O—. $R^3$ and $R^4$ are preferably each independently hydrogen, a halogen (fluorine, chlorine, bromine, or iodine), cyano, nitro, hydroxyl, a substituted or unsubstituted $C_1$-$C_6$ alkyl, a substituted or unsubstituted $C_2$-$C_6$ alkenyl, a substituted or unsubstituted $C_2$-$C_6$ alkynyl, a substituted or unsubstituted $C_3$-$C_6$ cycloalkyl, a substituted or unsubstituted $C_3$-$C_6$ cycloalkenyl, a substituted or unsubstituted $C_3$-$C_6$ cycloalkynyl, a substituted or unsubstituted 3 to 6-membered heterocycloalkyl, a substituted or unsubstituted $C_7$-$C_{11}$ cycloalkylalkyl, a substituted or unsubstituted 3 to 6-membered heterocycloalkyl-$C_1$-$C_6$ alkyl, a substituted or unsubstituted $C_6$-$C_{18}$ aryl, a substituted or unsubstituted $C_7$-$C_{20}$ arylalkyl, a substituted or unsubstituted 5 to 15-membered heteroaryl, a substituted or unsubstituted 5 to 15-membered heteroaryl-$C_1$-$C_6$ alkyl, a substituted or unsubstituted $C_1$-$C_6$ alkoxy, a substituted or unsubstituted $C_3$-$C_6$ cycloalkoxy, a substituted or unsubstituted 3 to 6-membered heterocycloalkoxy, a substituted or unsubstituted $C_6$-$C_{18}$ aryloxy, a substituted or unsubstituted $C_7$-$C_{20}$ arylalkyloxy, a substituted or unsubstituted $C_7$-$C_{20}$ arylalkenyloxy, a substituted or unsubstituted 5 to 15-membered heteroaryloxy, a substituted or unsubstituted 5 to 15-membered heteroaryl-$C_1$-$C_6$ alkyloxy, a substituted or unsubstituted $C_1$-$C_6$ alkoxycarbonyl, a substituted or unsubstituted $C_3$-$C_6$ cycloalkoxycarbonyl, a substituted or unsubstituted $C_1$-$C_{20}$ acyl, a substituted or unsubstituted $C_1$-$C_6$ alkylcarbonyloxy, a substituted or unsubstituted $C_6$-$C_{18}$ arylcarbonyloxy, a substituted or unsubstituted carbamoyl, a substituted or unsubstituted $C_1$-$C_6$ alkylsulfonyl, a substituted or unsubstituted $C_6$-$C_{18}$ arylsulfonyl, a substituted or unsubstituted $C_1$-$C_6$ alkylsulfanyl, a substituted or unsubstituted $C_6$-$C_{18}$ arylsulfanyl, or a substituted or unsubstituted amino, or they together form —O—$CR^5R^6$—O—; more preferably each independently hydrogen, hydroxyl, a substituted or unsubstituted $C_1$-$C_6$ alkoxy, a substituted or unsubstituted $C_1$-$C_6$ alkylcarbonyloxy, or a substituted or unsubstituted $C_6$-$C_{18}$ arylcarbonyloxy, or they together form —O—$CR^5R^6$—O—; further preferably each independently a substituted or unsubstituted $C_1$-$C_6$ alkylcarbonyloxy, or a substituted or unsubstituted $C_6$-$C_{18}$ arylcarbonyloxy, or they together form —O—$CR^5R^6$—O—; particularly preferably both acetoxy, or they together form —O—$CR^5R^6$—O—.

In formula (I), $R^5$ and $R^6$ are each independently hydrogen, a halogen (fluorine, chlorine, bromine, or iodine), cyano, nitro, hydroxyl, a substituted or unsubstituted alkyl, a substituted or unsubstituted alkenyl, a substituted or unsubstituted alkynyl, a substituted or unsubstituted cycloalkyl, a substituted or unsubstituted cycloalkenyl, a substituted or unsubstituted cycloalkynyl, a substituted or unsubstituted heterocycloalkyl, a substituted or unsubstituted cycloalkylalkyl, a substituted or unsubstituted heterocycloalkylalkyl, a substituted or unsubstituted aryl, a substituted or unsubstituted arylalkyl, a substituted or unsubstituted heteroaryl, a substituted or unsubstituted heteroarylalkyl, a substituted or unsubstituted alkoxy, a substituted or unsubstituted cycloalkoxy, a substituted or unsubstituted heterocycloalkoxy, a substituted or unsubstituted aryloxy, a substituted or unsubstituted arylalkyloxy, a substituted or unsubstituted arylalkenyloxy, a substituted or unsubstituted heteroaryloxy, a substituted or unsubstituted heteroarylalkyloxy, a substituted or unsubstituted alkoxycarbonyl, a substituted or unsubstituted cycloalkoxycarbonyl, a substituted or unsubstituted acyl, a substituted or unsubstituted alkylcarbonyloxy, a substituted or unsubstituted arylcarbonyloxy, a substituted or unsubstituted carbamoyl, a substituted or unsubstituted alkylsulfonyl, a substituted or unsubstituted arylsulfonyl, a substituted or unsubstituted alkylsulfanyl, a substituted or unsubstituted arylsulfanyl, or a substituted or unsubstituted amino. $R^5$ and $R^6$ are preferably each independently hydrogen, a halogen (fluorine, chlorine, bromine, or iodine), cyano, nitro, hydroxyl, a substituted or unsubstituted $C_1$-$C_6$ alkyl, a substituted or unsubstituted $C_2$-$C_6$ alkenyl, a substituted or unsubstituted $C_2$-$C_6$ alkynyl, a substituted or unsubstituted $C_3$-$C_6$ cycloalkyl, a substituted or unsubstituted $C_3$-$C_6$ cycloalkenyl, a substituted or unsubstituted $C_3$-$C_6$ cycloalkynyl, a substituted or unsubstituted 3 to 6-membered heterocycloalkyl, a substituted or unsubstituted $C_7$-$C_{11}$ cycloalkylalkyl, a substituted or unsubstituted 3 to 6-membered heterocycloalkyl-$C_1$-$C_6$ alkyl, a substituted or unsubstituted $C_6$-$C_{18}$ aryl, a substituted or unsubstituted $C_7$-$C_{20}$ arylalkyl, a substituted or unsubstituted 5 to 15-membered heteroaryl, a substituted or unsubstituted 5 to 15-membered heteroaryl-$C_1$-$C_6$ alkyl, a substituted or unsubstituted $C_1$-$C_6$ alkoxy, a substituted or unsubstituted $C_3$-$C_6$ cycloalkoxy, a substituted or unsubstituted 3 to 6-membered heterocycloalkoxy, a substituted or unsubstituted $C_6$-$C_{18}$ aryloxy, a substituted or unsubstituted $C_7$-$C_{20}$ arylalkyloxy, a substituted or unsubstituted $C_7$-$C_{20}$ arylalkenyloxy, a substituted or unsubstituted 5 to 15-membered heteroaryloxy, a substituted or unsubstituted 5 to 15-membered heteroaryl-$C_1$-$C_6$ alkyloxy, a substituted or unsubstituted $C_1$-$C_6$ alkoxycarbonyl, a substituted or unsubstituted $C_3$-$C_6$ cycloalkoxycarbonyl, a substituted or unsubstituted $C_1$-$C_{20}$ acyl, a substituted or unsubstituted $C_1$-$C_6$ alkylcarbonyloxy, a substituted or unsubstituted $C_6$-$C_{18}$ arylcarbonyloxy, a substituted or unsubstituted carbamoyl, a substituted or unsubstituted $C_1$-$C_6$ alkylsulfonyl, a substituted or unsubstituted $C_6$-$C_{18}$ arylsulfonyl, a substituted or unsubstituted $C_1$-$C_6$ alkylsulfanyl, a substituted or unsubstituted $C_6$-$C_{18}$ arylsulfanyl, or a substituted or unsubstituted amino; more preferably each independently hydrogen, a substituted or unsubstituted $C_1$-$C_6$ alkyl, a substituted or unsubstituted $C_2$-$C_6$ alkenyl, a substituted or unsubstituted $C_2$-$C_6$ alkynyl, a substituted or unsubstituted $C_3$-$C_6$ cycloalkyl, a substituted or unsubstituted $C_3$-$C_6$ cycloalkenyl, a substituted or unsubstituted $C_3$-$C_6$ cycloalkynyl, a substituted or unsubstituted 3 to 6-membered heterocycloalkyl, a substituted or unsubstituted $C_6$-$C_{18}$ aryl, a substituted or unsubstituted $C_7$-$C_{20}$ arylalkyl, a substituted or unsubstituted 5 to 15-membered heteroaryl, or a substituted or unsubstituted 5 to 15-membered heteroaryl-$C_1$-$C_6$ alkyl; further preferably each independently hydrogen, or a substituted or unsubstituted $C_6$-$C_{18}$ aryl; particularly preferably, $R^5$ is hydrogen, and $R^6$ is 2-methylphenyl.

According to one specific embodiment, at least one of $R^2$, $R^3$, $R^4$, $R^5$ and $R^6$ is preferably a substituted or unsubstituted aryl, a substituted or unsubstituted arylalkyl, a substituted or unsubstituted aryloxy, a substituted or unsubstituted arylalkyloxy, a substituted or unsubstituted arylalkenyloxy, a substituted or unsubstituted arylcarbonyloxy, a substituted or unsubstituted arylsulfonyl, or a substituted or unsubstituted arylsulfanyl, and the remaining groups out of $R^2$, $R^3$, $R^4$, $R^5$, and $R^6$ are groups defined above. In the case of this embodiment, at least one of $R^2$, $R^3$, $R^4$, $R^5$ and $R^6$ is preferably a substituted or unsubstituted $C_6$-$C_{18}$ aryl, a substituted or unsubstituted $C_7$-$C_{20}$ arylalkyl, a substituted or unsubstituted $C_6$-$C_{18}$ aryloxy, a substituted or unsubstituted $C_7$-$C_{20}$ arylalkyloxy, a substituted or unsubstituted $C_7$-$C_{20}$ arylalkenyloxy, a substituted or unsubstituted $C_6$-$C_{18}$ arylcarbonyloxy, a substituted or unsubstituted $C_6$-$C_{18}$ arylsulfonyl, or a substituted or unsubstituted $C_6$-$C_{18}$ arylsulfanyl, and the remaining groups out of $R^2$, $R^3$, $R^4$, $R^5$, and $R^6$ are groups defined above; more preferably at least one of $R^2$, $R^3$, $R^4$, $R^5$ and $R^6$ is a substituted or unsubstituted $C_6$-$C_{18}$ aryl, a substituted or unsubstituted $C_7$-$C_{20}$ arylalkyl, or a substituted or unsubstituted $C_6$-$C_{18}$ arylcarbonyloxy, and the remaining groups out of $R^2$, $R^3$, $R^4$, $R^5$, and $R^6$ are groups defined above; further preferably, at least one of $R^2$, $R^3$, $R^4$, $R^5$ and $R^6$ is a substituted or unsubstituted $C_6$-$C_{18}$ aryl, or a substituted or unsubstituted $C_6$-$C_{18}$ arylcarbonyloxy, and the remaining groups out of $R^2$, $R^3$, $R^4$, $R^5$, and $R^6$ are groups defined above; particularly preferably, $R^2$ is 4-cyanobenzoyloxy, $R^3$ and $R^4$ are both acetoxy or together form —O—$CR^5R^6$—O—, $R^5$ is hydrogen, and $R^6$ is 2-methylphenyl.

In formula (I), in the case where the groups are substituted, the substituents are preferably each independently at least one monovalent group or divalent group selected from the group consisting of a halogen (fluorine, chlorine, bromine or iodine), cyano, nitro, hydroxyl, a substituted or unsubstituted alkyl, a substituted or unsubstituted alkenyl, a substituted or unsubstituted alkynyl, a substituted or unsubstituted cycloalkyl, a substituted or unsubstituted cycloalkenyl, a substituted or unsubstituted cycloalkynyl, a substituted or unsubstituted heterocycloalkyl, a substituted or unsubstituted cycloalkylalkyl, a substituted or unsubstituted heterocycloalkylalkyl, a substituted or unsubstituted aryl, a substituted or unsubstituted arylalkyl, a substituted or unsubstituted heteroaryl, a substituted or unsubstituted heteroarylalkyl, a substituted or unsubstituted alkoxy, a substituted or unsubstituted cycloalkoxy, a substituted or unsubstituted heterocycloalkoxy, a substituted or unsubstituted aryloxy, a substituted or unsubstituted arylalkyloxy, a substituted or unsubstituted heteroaryloxy, a substituted or unsubstituted heteroarylalkyloxy, a substituted or unsubstituted alkoxycarbonyl, a substituted or unsubstituted cycloalkoxycarbonyl, a substituted or unsubstituted acyl, a substituted or unsubstituted acyloxy, a substituted or unsubstituted amino, and oxo (C═O), more preferably at least one monovalent group or divalent group selected from the group consisting of a halogen (fluorine, chlorine, bromine or iodine), cyano, nitro, hydroxyl, a substituted or unsubstituted $C_1$-$C_6$ alkyl, a substituted or unsubstituted $C_2$-$C_6$ alkenyl, a substituted or unsubstituted $C_2$-$C_6$ alkynyl, a substituted or unsubstituted $C_3$-$C_6$ cycloalkyl, a substituted or unsubstituted $C_4$-$C_6$ cycloalkenyl, a substituted or unsubstituted $C_4$-$C_6$ cycloalkynyl, a substituted or unsubstituted 3 to 6-membered heterocycloalkyl, a substituted or unsubstituted $C_7$-$C_{11}$ cycloalkylalkyl, a substituted or unsubstituted 3 to 6-membered heterocycloalkyl-$C_1$-$C_6$ alkyl, a substituted or unsubstituted $C_6$-$C_{18}$ aryl, a substituted or unsubstituted $C_7$-$C_{20}$ arylalkyl, a substituted or unsubstituted 5 to 15-membered heteroaryl, a substituted or unsubstituted 5 to 15-membered heteroaryl-$C_1$-$C_6$ alkyl, a substituted or unsubstituted $C_1$-$C_6$ alkoxy, a substituted or unsubstituted $C_3$-$C_6$ cycloalkoxy, a substituted or unsubstituted 3 to 6-membered heterocycloalkoxy, a substituted or unsubstituted $C_6$-$C_{18}$ aryloxy, a substituted or unsubstituted $C_7$-$C_{20}$ arylalkyloxy, a substituted or unsubstituted 5 to 15-membered heteroaryloxy, a substituted or unsubstituted 5 to 15-membered heteroaryl-$C_1$-$C_6$ alkyloxy, a substituted or unsubstituted $C_1$-$C_6$ alkoxycarbonyl, a substituted or unsubstituted $C_3$-$C_6$ cycloalkoxycarbonyl, a substituted or unsubstituted $C_1$-$C_{20}$ acyl, a substituted or unsubstituted $C_1$-$C_{20}$ acyloxy, a substituted or unsubstituted amino, and oxo (C═O), further preferably at least one monovalent group selected from the group consisting of hydroxyl, a substituted or unsubstituted $C_1$-$C_6$ alkoxy, a substituted or unsubstituted $C_3$-$C_6$ cycloalkoxy, a substituted or unsubstituted 3 to 6-membered heterocycloalkoxy, a substituted or unsubstituted $C_6$-$C_{18}$ aryloxy, a substituted or unsubstituted $C_7$-$C_{20}$ arylalkyloxy, a substituted or unsubstituted 5 to 15-membered heteroaryloxy, a substituted or unsubstituted 5 to 15-membered heteroaryl-$C_1$-$C_6$ alkyloxy, and substituted or unsubstituted $C_1$-$C_{20}$ acyloxy, particularly preferably hydroxyl. In the case where the monovalent group is substituted, the substituent is preferably further selected from the monovalent groups or divalent groups described above, more preferably further selected from the unsubstituted monovalent groups or divalent groups described above.

The compound represented by formula (I) can include a compound defined by any combination of n, $R^1$, $R^2$, $R^3$, $R^4$, $R^5$, and $R^6$ exemplified above, provided that the case where n is 1, and $R^2$, $R^3$, and $R^4$ are acetoxy is excepted from the compound of the formula (I). The compound in which n is 1, and $R^2$, $R^3$, and $R^4$ is acetoxy, in formula (I) is pyripyropene A. In the case where n, $R^1$, $R^2$, $R^3$, $R^4$, $R^5$, and $R^6$ is a group exemplified above, the compound represented by formula (I) can exert high inhibitory activity on the functions of PCSK9.

Preferably, the compound represented by formula (I) is a compound, wherein:

$R^1$ is a substituted or unsubstituted $C_3$-$C_6$ cycloalkyl, a substituted or unsubstituted 3 to 6-membered heterocycloalkyl, a substituted or unsubstituted $C_6$-$C_{18}$ aryl, or a substituted or unsubstituted 5 to 15-membered heteroaryl;

$R^2$ is hydrogen, a halogen (fluorine, chlorine, bromine, or iodine), cyano, nitro, hydroxyl, a substituted or unsubstituted $C_1$-$C_6$ alkyl, a substituted or unsubstituted $C_2$-$C_6$ alkenyl, a substituted or unsubstituted $C_2$-$C_6$ alkynyl, a substituted or unsubstituted $C_3$-$C_6$ cycloalkyl, a substituted or unsubstituted $C_3$-$C_6$ cycloalkenyl, a substituted or unsubstituted $C_3$-$C_6$ cycloalkynyl, a substituted or unsubstituted 3 to 6-membered heterocycloalkyl, a substituted or unsubstituted $C_7$-$C_{11}$ cycloalkylalkyl, a substituted or unsubstituted 3 to 6-membered heterocycloalkyl-$C_1$-$C_6$ alkyl, a substituted or unsubstituted $C_6$-$C_{18}$ aryl, a substituted or unsubstituted $C_7$-$C_{20}$ arylalkyl, a substituted or unsubstituted 5 to 15-membered heteroaryl, a substituted or unsubstituted 5 to 15-membered heteroaryl-$C_1$-$C_6$ alkyl, a substituted or unsubstituted $C_1$-$C_6$ alkoxy, a substituted or unsubstituted $C_3$-$C_6$ cycloalkoxy, a substituted or unsubstituted 3 to 6-membered heterocycloalkoxy, a substituted or unsubstituted $C_6$-$C_{18}$ aryloxy, a substituted or unsubstituted $C_7$-$C_{20}$ arylalkyloxy, a substituted or unsubstituted $C_7$-$C_{20}$ arylalkenyloxy, a substituted or unsubstituted 5 to 15-membered heteroaryloxy, a substituted or unsubstituted 5 to 15-membered heteroaryl-$C_1$-$C_6$ alkyloxy, a substituted or unsubstituted $C_1$-$C_6$ alkoxycarbonyl, a substituted or unsubstituted $C_3$-$C_6$ cycloalkoxycarbonyl, a substituted or unsubstituted $C_1$-$C_{20}$ acyl, a substituted or unsubstituted $C_1$-$C_6$ alkylcarbonyloxy, a substituted or unsubstituted $C_6$-$C_{18}$ arylcarbonyloxy, a substituted or unsubstituted carbamoyl, a substituted or unsubstituted $C_1$-$C_6$ alkylsulfonyl, a substituted or unsubstituted $C_6$-$C_{18}$ arylsulfonyl, a substituted or unsubstituted $C_1$-$C_6$ alkylsulfanyl, a substituted or unsubstituted $C_6$-$C_{18}$ arylsulfanyl, or a substituted or unsubstituted amino;

n is 1;

$R^3$ and $R^4$ are each independently hydrogen, a halogen (fluorine, chlorine, bromine, or iodine), cyano, nitro, hydroxyl, a substituted or unsubstituted $C_1$-$C_6$ alkyl, a substituted or unsubstituted $C_2$-$C_6$ alkenyl, a substituted or unsubstituted $C_2$-$C_6$ alkynyl, a substituted or unsubstituted $C_3$-$C_6$ cycloalkyl, a substituted or unsubstituted $C_3$-$C_6$ cycloalkenyl, a substituted or unsubstituted $C_3$-$C_6$ cycloalkynyl, a substituted or unsubstituted 3 to 6-membered heterocycloalkyl, a substituted or unsubstituted $C_7$-$C_{11}$ cycloalkylalkyl, a substituted or unsubstituted 3 to 6-membered heterocycloalkyl-$C_1$-$C_6$ alkyl, a substituted or unsubstituted $C_6$-$C_{18}$ aryl, a substituted or unsubstituted $C_7$-$C_{20}$ arylalkyl, a substituted or unsubstituted 5 to 15-membered heteroaryl, a substituted or unsubstituted 5 to 15-membered heteroaryl-$C_1$-$C_6$ alkyl, a substituted or unsubstituted $C_1$-$C_6$ alkoxy, a substituted or unsubstituted $C_3$-$C_6$ cycloalkoxy, a substituted or unsubstituted 3 to 6-membered heterocycloalkoxy, a substituted or unsubstituted $C_6$-$C_{18}$ aryloxy, a substituted or unsubstituted $C_7$-$C_{20}$ arylalkyloxy, a substituted or unsubstituted $C_7$-$C_{20}$ arylalkenyloxy, a substituted or unsubstituted 5 to 15-membered heteroaryloxy, a substituted or unsubstituted 5 to 15-membered heteroaryl-$C_1$-$C_6$ alkyloxy, a substituted or unsubstituted $C_1$-$C_6$ alkoxycarbonyl, a substituted or unsubstituted $C_3$-$C_6$ cycloalkoxycarbonyl, a substituted or unsubstituted $C_1$-$C_{20}$ acyl, a substituted or unsubstituted $C_1$-$C_6$ alkylcarbonyloxy, a substituted or unsubstituted $C_6$-$C_{18}$ arylcarbonyloxy, a substituted or unsubstituted carbamoyl, a substituted or unsubstituted $C_1$-$C_6$ alkylsulfonyl, a substituted or unsubstituted $C_6$-$C_{18}$ arylsulfonyl, a substituted or unsubstituted $C_1$-$C_6$ alkylsulfanyl, a substituted or unsubstituted $C_6$-$C_{18}$ arylsulfanyl, or a substituted or unsubstituted amino, or $R^3$ and $R^4$ together form —O—$CR^5R^6$—O—; wherein:

$R^5$ and $R^6$ are each independently hydrogen, a halogen (fluorine, chlorine, bromine, or iodine), cyano, nitro, hydroxyl, a substituted or unsubstituted $C_1$-$C_6$ alkyl, a substituted or unsubstituted $C_2$-$C_6$ alkenyl, a substituted or unsubstituted $C_2$-$C_6$ alkynyl, a substituted or unsubstituted $C_3$-$C_6$ cycloalkyl, a substituted or unsubstituted $C_3$-$C_6$ cycloalkenyl, a substituted or unsubstituted $C_3$-$C_6$ cycloalkynyl, a substituted or unsubstituted 3 to 6-membered heterocycloalkyl, a substituted or unsubstituted $C_7$-$C_{11}$ cycloalkylalkyl, a substituted or unsubstituted 3 to 6-membered heterocycloalkyl-$C_1$-$C_6$ alkyl, a substituted or unsubstituted $C_6$-$C_{18}$ aryl, a substituted or unsubstituted $C_7$-$C_{20}$ arylalkyl, a substituted or unsubstituted 5 to 15-membered heteroaryl, a substituted or unsubstituted 5 to 15-membered heteroaryl-$C_1$-$C_6$ alkyl, a substituted or unsubstituted $C_1$-$C_6$ alkoxy, a substituted or unsubstituted $C_3$-$C_6$ cycloalkoxy, a substituted or unsubstituted 3 to 6-membered heterocycloalkoxy, a substituted or unsubstituted $C_6$-$C_{18}$ aryloxy, a substituted or unsubstituted $C_7$-$C_{20}$ arylalkyloxy, a substituted or unsubstituted $C_7$-$C_{20}$ arylalkenyloxy, a substituted or unsubstituted 5 to 15-membered heteroaryloxy, a substituted or unsubstituted 5 to 15-membered heteroaryl-$C_1$-$C_6$ alkyloxy, a substituted or unsubstituted $C_1$-$C_6$ alkoxycarbonyl, a substituted or unsubstituted $C_3$-$C_6$ cycloalkoxycarbonyl, a substituted or unsubstituted $C_1$-$C_{20}$ acyl, a substituted or unsubstituted $C_1$-$C_6$ alkylcarbonyloxy, a substituted or unsubstituted $C_6$-$C_{18}$ arylcarbonyloxy, a substituted or unsubstituted carbamoyl, a substituted or unsubstituted $C_1$-$C_6$ alkylsulfonyl, a substituted or unsubstituted $C_6$-$C_{18}$ arylsulfonyl, a substituted or unsubstituted $C_1$-$C_6$ alkylsulfanyl, a substituted or unsubstituted $C_6$-$C_{18}$ arylsulfanyl, or a substituted or unsubstituted amino;

provided that the case where n is 1, and $R^2$, $R^3$, and $R^4$ are acetoxy is excepted; and in the case where the groups are substituted, the substituents are each independently at least one monovalent group or divalent group selected from the group consisting of a halogen (fluorine, chlorine, bromine or iodine), cyano, nitro, hydroxyl, a substituted or unsubstituted $C_1$-$C_6$ alkyl, a substituted or unsubstituted $C_2$-$C_6$ alkenyl, a substituted or unsubstituted $C_2$-$C_6$ alkynyl, a substituted or unsubstituted $C_3$-$C_6$ cycloalkyl, a substituted or unsubstituted $C_4$-$C_6$ cycloalkenyl, a substituted or unsubstituted $C_4$-$C_6$ cycloalkynyl, a substituted or unsubstituted 3 to 6-membered heterocycloalkyl, a substituted or unsubstituted $C_7$-$C_{11}$ cycloalkylalkyl, a substituted or unsubstituted 3 to 6-membered heterocycloalkyl-$C_1$-$C_6$ alkyl, a substituted or unsubstituted $C_6$-$C_{18}$ aryl, a substituted or unsubstituted $C_7$-$C_{20}$ arylalkyl, a substituted or unsubstituted 5 to 15-membered heteroaryl, a substituted or unsubstituted 5 to 15-membered heteroaryl-$C_1$-$C_6$ alkyl, a substituted or unsubstituted $C_1$-$C_6$ alkoxy, a substituted or unsubstituted $C_3$-$C_6$ cycloalkoxy, a substituted or unsubstituted 3 to 6-membered heterocycloalkoxy, a substituted or unsubstituted $C_6$-$C_{18}$ aryloxy, a substituted or unsubstituted $C_7$-$C_{20}$ arylalkyloxy, a substituted or unsubstituted 5 to 15-membered heteroaryloxy, a substituted or unsubstituted 5 to 15-membered heteroaryl-$C_1$-$C_6$ alkyloxy, a substituted or unsubstituted $C_1$-$C_6$ alkoxycarbonyl, a substituted or unsubstituted $C_3$-$C_6$ cycloalkoxycarbonyl, a substituted or unsubstituted $C_1$-$C_{20}$ acyl, a substituted or unsubstituted $C_1$-$C_{20}$ acyloxy, a substituted or unsubstituted amino, and oxo (C═O). In the case where the monovalent group is substituted, the substituent is preferably further selected from the monovalent groups or divalent groups described above, more preferably further selected from the unsubstituted monovalent groups or divalent groups described above.

More preferably, the compound represented by formula (I) is a compound, wherein:

$R^1$ is a substituted or unsubstituted 5 to 15-membered heteroaryl;

$R^2$ is hydrogen, hydroxyl, a substituted or unsubstituted $C_1$-$C_6$ alkoxy, a substituted or unsubstituted $C_1$-$C_6$ alkylcarbonyloxy, or a substituted or unsubstituted $C_6$-$C_{18}$ arylcarbonyloxy;

n is 1;

$R^3$ and $R^4$ are each independently hydrogen, hydroxyl, a substituted or unsubstituted $C_1$-$C_6$ alkoxy, a substituted or unsubstituted $C_1$-$C_6$ alkylcarbonyloxy, or a substituted or unsubstituted $C_6$-$C_{18}$ arylcarbonyloxy, or $R^3$ and $R^4$ together form —O—$CR^5R^6$—O—; wherein:

$R^5$ and $R^6$ are each independently hydrogen, a substituted or unsubstituted $C_1$-$C_6$ alkyl, a substituted or unsubstituted $C_2$-$C_6$ alkenyl, a substituted or unsubstituted $C_2$-$C_6$ alkynyl, a substituted or unsubstituted $C_3$-$C_6$ cycloalkyl, a substituted or unsubstituted $C_3$-$C_6$ cycloalkenyl, a substituted or unsubstituted $C_3$-$C_6$ cycloalkynyl, a substituted or unsubstituted 3 to 6-membered heterocycloalkyl, a substituted or unsubstituted $C_6$-$C_{18}$ aryl, a substituted or unsubstituted $C_7$-$C_{20}$ arylalkyl, a substituted or unsubstituted 5 to 15-membered heteroaryl, or a substituted or unsubstituted 5 to 15-membered heteroaryl-$C_1$-$C_6$ alkyl;

provided that the case where n is 1, and $R^2$, $R^3$, and $R^4$ are acetoxy is excepted; and in the case where the groups are substituted, the substituents are each independently at least one monovalent group or divalent group selected from the group consisting of a halogen (fluorine, chlorine, bromine or iodine), cyano, nitro, hydroxyl, a substituted or unsubstituted $C_1$-$C_6$ alkyl, a substituted or unsubstituted $C_2$-$C_6$ alkenyl, a substituted or unsubstituted $C_2$-$C_6$ alkynyl, a substituted or unsubstituted $C_3$-$C_6$ cycloalkyl, a substituted or unsubstituted $C_4$-$C_6$ cycloalkenyl, a substituted or unsubstituted $C_4$-$C_6$ cycloalkynyl, a substituted or unsubstituted 3 to 6-membered heterocycloalkyl, a substituted or unsubstituted $C_7$-$C_{11}$ cycloalkylalkyl, a substituted or unsubstituted 3 to 6-membered heterocycloalkyl-$C_1$-$C_6$ alkyl, a substituted or unsubstituted $C_6$-$C_{18}$ aryl, a substituted or unsubstituted $C_7$-$C_{20}$ arylalkyl, a substituted or unsubstituted 5 to 15-membered heteroaryl, a substituted or unsubstituted 5 to 15-membered heteroaryl-$C_1$-$C_6$ alkyl, a substituted or unsubstituted $C_1$-$C_6$ alkoxy, a substituted or unsubstituted $C_3$-$C_6$ cycloalkoxy, a substituted or unsubstituted 3 to 6-membered heterocycloalkoxy, a substituted or unsubstituted $C_6$-$C_{18}$ aryloxy, a substituted or unsubstituted $C_7$-$C_{20}$ arylalkyloxy, a substituted or unsubstituted 5 to 15-membered heteroaryloxy, a substituted or unsubstituted 5 to 15-membered heteroaryl-$C_1$-$C_6$ alkyloxy, a substituted or unsubstituted $C_1$-$C_6$ alkoxycarbonyl, a substituted or unsubstituted $C_3$-$C_6$ cycloalkoxycarbonyl, a substituted or unsubstituted $C_1$-$C_{20}$ acyl, a substituted or unsubstituted $C_1$-$C_{20}$ acyloxy, a substituted or unsubstituted amino, and oxo (C═O). In the case where the monovalent group is substituted, the substituent is preferably further selected from the monovalent groups or divalent groups described above, more preferably further selected from the unsubstituted monovalent groups or divalent groups described above.

Further preferably, the compound represented by formula (I) is a compound, wherein:

$R^4$ is a substituted or unsubstituted 5 to 15-membered heteroaryl;

$R^2$ is a substituted or unsubstituted $C_1$-$C_6$ alkylcarbonyloxy, or a substituted or unsubstituted $C_6$-$C_{18}$ arylcarbonyloxy;

n is 1;

$R^3$ and $R^4$ are each independently a substituted or unsubstituted $C_1$-$C_6$ alkylcarbonyloxy, or a substituted or unsubstituted $C_6$-$C_{18}$ arylcarbonyloxy, or $R^3$ and $R^4$ together form —O—$CR^5R^6$—O—; wherein:

$R^5$ and $R^6$ are each independently hydrogen, or a substituted or unsubstituted $C_6$-$C_{18}$ aryl;

provided that the case where n is 1, and $R^2$, $R^3$, and $R^4$ are acetoxy is excepted; and in the case where the groups are substituted, the substituents are each independently at least one monovalent group or divalent group selected from the group consisting of a halogen (fluorine, chlorine, bromine or iodine), cyano, nitro, hydroxyl, a substituted or unsubstituted $C_1$-$C_6$ alkyl, a substituted or unsubstituted $C_2$-$C_6$ alkenyl, a substituted or unsubstituted $C_2$-$C_6$ alkynyl, a substituted or unsubstituted $C_3$-$C_6$ cycloalkyl, a substituted or unsubstituted $C_4$-$C_6$ cycloalkenyl, a substituted or unsubstituted $C_4$-$C_6$ cycloalkynyl, a substituted or unsubstituted 3 to 6-membered heterocycloalkyl, a substituted or unsubstituted $C_7$-$C_{11}$ cycloalkylalkyl, a substituted or unsubstituted 3 to 6-membered heterocycloalkyl-$C_1$-$C_6$ alkyl, a substituted or unsubstituted $C_6$-$C_{18}$ aryl, a substituted or unsubstituted $C_7$-$C_{20}$ arylalkyl, a substituted or unsubstituted 5 to 15-membered heteroaryl, a substituted or unsubstituted 5 to 15-membered heteroaryl-$C_1$-$C_6$ alkyl, a substituted or unsubstituted $C_1$-$C_6$ alkoxy, a substituted or unsubstituted $C_3$-$C_6$ cycloalkoxy, a substituted or unsubstituted 3 to 6-membered heterocycloalkoxy, a substituted or unsubstituted $C_6$-$C_{18}$ aryloxy, a substituted or unsubstituted $C_7$-$C_{20}$ arylalkyloxy, a substituted or unsubstituted 5 to 15-membered heteroaryloxy, a substituted or unsubstituted 5 to 15-membered heteroaryl-$C_1$-$C_6$ alkyloxy, a substituted or unsubstituted $C_1$-$C_6$ alkoxycarbonyl, a substituted or unsubstituted $C_3$-$C_6$ cycloalkoxycarbonyl, a substituted or unsubstituted $C_1$-$C_{20}$ acyl, a substituted or unsubstituted $C_1$-$C_{20}$ acyloxy, a substituted or unsubstituted amino, and oxo (C═O). In the case where the monovalent group is substituted, the substituent is preferably further selected from the monovalent groups or divalent groups described above, more preferably further selected from the unsubstituted monovalent groups or divalent groups described above.

According to one specific embodiment, the compound represented by formula (I) is a compound, wherein:

$R^1$ is a substituted or unsubstituted $C_3$-$C_6$ cycloalkyl, a substituted or unsubstituted 3 to 6-membered heterocycloalkyl, a substituted or unsubstituted $C_6$-$C_{18}$ aryl, or a substituted or unsubstituted 5 to 15-membered heteroaryl;

$R^2$ is hydrogen, a halogen (fluorine, chlorine, bromine, or iodine), cyano, nitro, hydroxyl, a substituted or unsubstituted $C_1$-$C_6$ alkyl, a substituted or unsubstituted $C_2$-$C_6$ alkenyl, a substituted or unsubstituted $C_2$-$C_6$ alkynyl, a substituted or unsubstituted $C_3$-$C_6$ cycloalkyl, a substituted or unsubstituted $C_3$-$C_6$ cycloalkenyl, a substituted or unsubstituted $C_3$-$C_6$ cycloalkynyl, a substituted or unsubstituted 3 to 6-membered heterocycloalkyl, a substituted or unsubstituted $C_7$-$C_{11}$ cycloalkylalkyl, a substituted or unsubstituted 3 to 6-membered heterocycloalkyl-$C_1$-$C_6$ alkyl, a substituted or unsubstituted $C_6$-$C_{18}$ aryl, a substituted or unsubstituted $C_7$-$C_{20}$ arylalkyl, a substituted or unsubstituted 5 to 15-membered heteroaryl, a substituted or unsubstituted 5 to 15-membered heteroaryl-$C_1$-$C_6$ alkyl, a substituted or unsubstituted $C_1$-$C_6$ alkoxy, a substituted or unsubstituted $C_3$-$C_6$ cycloalkoxy, a substituted or unsubstituted 3 to 6-membered heterocycloalkoxy, a substituted or unsubstituted $C_6$-$C_{18}$ aryloxy, a substituted or unsubstituted $C_7$-$C_{20}$ arylalkyloxy, a substituted or unsubstituted $C_7$-$C_{20}$ arylalkenyloxy, a substituted or unsubstituted 5 to 15-membered heteroaryloxy, a substituted or unsubstituted 5 to 15-membered heteroaryl-$C_1$-$C_6$ alkyloxy, a substituted or unsubstituted $C_1$-$C_6$ alkoxycarbonyl, a substituted or unsubstituted $C_3$-$C_6$ cycloalkoxycarbonyl, a substituted or unsubstituted $C_1$-$C_{20}$ acyl, a substituted or unsubstituted $C_1$-$C_6$ alkylcarbonyloxy, a substituted or unsubstituted $C_6$-$C_{18}$ arylcarbonyloxy, a substituted or unsubstituted carbamoyl, a substituted or unsubstituted $C_1$-$C_6$ alkylsulfonyl, a substituted or unsubstituted $C_6$-$C_{18}$ arylsulfonyl, a substituted or unsubstituted $C_1$-$C_6$ alkylsulfanyl, a substituted or unsubstituted $C_6$-$C_{18}$ arylsulfanyl, or a substituted or unsubstituted amino;

n is 1;

$R^3$ and $R^4$ are each independently hydrogen, a halogen (fluorine, chlorine, bromine, or iodine), cyano, nitro, hydroxyl, a substituted or unsubstituted $C_1$-$C_6$ alkyl, a substituted or unsubstituted $C_2$-$C_6$ alkenyl, a substituted or unsubstituted $C_2$-$C_6$ alkynyl, a substituted or unsubstituted $C_3$-$C_6$ cycloalkyl, a substituted or unsubstituted $C_3$-$C_6$ cycloalkenyl, a substituted or unsubstituted $C_3$-$C_6$ cycloalkynyl, a substituted or unsubstituted 3 to 6-membered heterocycloalkyl, a substituted or unsubstituted $C_7$-$C_{11}$ cycloalkylalkyl, a substituted or unsubstituted 3 to 6-membered heterocycloalkyl-$C_1$-$C_6$ alkyl, a substituted or unsubstituted $C_6$-$C_{18}$ aryl, a substituted or unsubstituted $C_7$-$C_{20}$ arylalkyl, a substituted or unsubstituted 5 to 15-membered heteroaryl, a substituted or unsubstituted 5 to 15-membered heteroaryl-$C_1$-$C_6$ alkyl, a substituted or unsubstituted $C_1$-$C_6$ alkoxy, a substituted or unsubstituted $C_3$-$C_6$ cycloalkoxy, a substituted or unsubstituted 3 to 6-membered heterocycloalkoxy, a substituted or unsubstituted $C_6$-$C_{18}$ aryloxy, a substituted or unsubstituted $C_7$-$C_{20}$ arylalkyloxy, a substituted or unsubstituted $C_7$-$C_{20}$ arylalkenyloxy, a substituted or unsubstituted 5 to 15-membered heteroaryloxy, a substituted or unsubstituted 5 to 15-membered heteroaryl-$C_1$-$C_6$ alkyloxy, a substituted or unsubstituted $C_1$-$C_6$ alkoxycarbonyl, a substituted or unsubstituted $C_3$-$C_6$ cycloalkoxycarbonyl, a substituted or unsubstituted $C_1$-$C_{20}$ acyl, a substituted or unsubstituted $C_1$-$C_6$ alkylcarbonyloxy, a substituted or unsubstituted $C_6$-$C_{18}$ arylcarbonyloxy, a substituted or unsubstituted carbamoyl, a substituted or unsubstituted $C_1$-$C_6$ alkylsulfonyl, a substituted or unsubstituted $C_6$-$C_{18}$ arylsulfonyl, a substituted or unsubstituted $C_1$-$C_6$ alkylsulfanyl, a substituted or unsubstituted $C_6$-$C_{18}$ arylsulfanyl, or a substituted or unsubstituted amino, or $R^3$ and $R^4$ together form —O—$CR^5R^6$—O—; wherein:

$R^5$ and $R^6$ are each independently hydrogen, a halogen (fluorine, chlorine, bromine, or iodine), cyano, nitro, hydroxyl, a substituted or unsubstituted $C_1$-$C_6$ alkyl, a substituted or unsubstituted $C_2$-$C_6$ alkenyl, a substituted or unsubstituted $C_2$-$C_6$ alkynyl, a substituted or unsubstituted $C_3$-$C_6$ cycloalkyl, a substituted or unsubstituted $C_3$-$C_6$ cycloalkenyl, a substituted or unsubstituted $C_3$-$C_6$ cycloalkynyl, a substituted or unsubstituted 3 to 6-membered heterocycloalkyl, a substituted or unsubstituted $C_7$-$C_{11}$ cycloalkylalkyl, a substituted or unsubstituted 3 to 6-membered heterocycloalkyl-$C_1$-$C_6$ alkyl, a substituted or unsubstituted $C_6$-$C_{18}$ aryl, a substituted or unsubstituted $C_7$-$C_{20}$ arylalkyl, a substituted or unsubstituted 5 to 15-membered heteroaryl, a substituted or unsubstituted 5 to 15-membered heteroaryl-$C_1$-$C_6$ alkyl, a substituted or unsubstituted $C_1$-$C_6$ alkoxy, a substituted or unsubstituted $C_3$-$C_6$ cycloalkoxy, a substituted or unsubstituted 3 to 6-membered heterocycloalkoxy, a substituted or unsubstituted $C_6$-$C_{18}$ aryloxy, a substituted or unsubstituted $C_7$-$C_{20}$ arylalkyloxy, a substituted or unsubstituted $C_7$-$C_{20}$ arylalkenyloxy, a substituted or unsubstituted 5 to 15-membered heteroaryloxy, a substituted or unsubstituted 5 to 15-membered heteroaryl-$C_1$-$C_6$ alkyloxy, a substituted or unsubstituted $C_1$-$C_6$ alkoxycarbonyl, a substituted or unsubstituted $C_3$-$C_6$ cycloalkoxycarbonyl, a substituted or unsubstituted $C_1$-$C_{20}$ acyl, a substituted or unsubstituted $C_1$-$C_6$ alkylcarbonyloxy, a substituted or unsubstituted $C_6$-$C_{18}$ arylcarbonyloxy, a substituted or unsubstituted carbamoyl, a substituted or unsubstituted $C_1$-$C_6$ alkylsulfonyl, a substituted or unsubstituted $C_6$-$C_{18}$ arylsulfonyl, a substituted or unsubstituted $C_1$-$C_6$ alkylsulfanyl, a substituted or unsubstituted $C_6$-$C_{18}$ arylsulfanyl, or a substituted or unsubstituted amino;

provided that at least one of $R^2$, $R^3$, $R^4$, $R^5$, and $R^6$ is a substituted or unsubstituted $C_6$-$C_{18}$ aryl, a substituted or unsubstituted $C_7$-$C_{20}$ arylalkyl, a substituted or unsubstituted $C_6$-$C_{18}$ aryloxy, a substituted or unsubstituted $C_7$-$C_{20}$ arylalkyloxy, a substituted or unsubstituted $C_7$-$C_{20}$ arylalkenyloxy, a substituted or unsubstituted $C_6$-$C_{18}$ arylcarbonyloxy, a substituted or unsubstituted $C_6$-$C_{18}$ arylsulfonyl, or a substituted or unsubstituted $C_6$-$C_{18}$ arylsulfanyl, and the remaining groups out of $R^2$, $R^3$, $R^4$, $R^5$, and $R^6$ are groups defined above; and in the case where the groups are substituted, the substituents are each independently at least one monovalent group or divalent group selected from the group consisting of a halogen (fluorine, chlorine, bromine or iodine), cyano, nitro, hydroxyl, a substituted or unsubstituted $C_1$-$C_6$ alkyl, a substituted or unsubstituted $C_2$-$C_6$ alkenyl, a substituted or unsubstituted $C_2$-$C_6$ alkynyl, a substituted or unsubstituted $C_3$-$C_6$ cycloalkyl, a substituted or unsubstituted $C_4$-$C_6$ cycloalkenyl, a substituted or unsubstituted $C_4$-$C_6$ cycloalkynyl, a substituted or unsubstituted 3 to 6-membered heterocycloalkyl, a substituted or unsubstituted $C_7$-$C_{11}$ cycloalkylalkyl, a substituted or unsubstituted 3 to 6-membered heterocycloalkyl-$C_1$-$C_6$ alkyl, a substituted or unsubstituted $C_6$-$C_{18}$ aryl, a substituted or unsubstituted $C_7$-$C_{20}$ arylalkyl, a substituted or unsubstituted 5 to 15-membered heteroaryl, a substituted or unsubstituted 5 to 15-membered heteroaryl-$C_1$-$C_6$ alkyl, a substituted or unsubstituted $C_1$-$C_6$ alkoxy, a substituted or unsubstituted $C_3$-$C_6$ cycloalkoxy, a substituted or unsubstituted 3 to 6-membered heterocycloalkoxy, a substituted or unsubstituted $C_6$-$C_{18}$ aryloxy, a substituted or unsubstituted $C_7$-$C_{20}$ arylalkyloxy, a substituted or unsubstituted 5 to 15-membered heteroaryloxy, a substituted or unsubstituted 5 to 15-membered heteroaryl-$C_1$-$C_6$ alkyloxy, a substituted or unsubstituted $C_1$-$C_6$ alkoxycarbonyl, a substituted or unsubstituted $C_3$-$C_6$ cycloalkoxycarbonyl, a substituted or unsubstituted $C_1$-$C_{20}$ acyl, a substituted or unsubstituted $C_1$-$C_{20}$ acyloxy, a substituted or unsubstituted amino, and oxo (C═O). In the case where the monovalent group is substituted, the substituent is preferably further selected from the monovalent groups or divalent groups described above, more preferably further selected from the unsubstituted monovalent groups or divalent groups described above.

According to one specific embodiment, more preferably, the compound represented by formula (I) is a compound, wherein:

- $R^1$ is a substituted or unsubstituted 5 to 15-membered heteroaryl;
- $R^2$ is hydrogen, hydroxyl, a substituted or unsubstituted $C_1$-$C_6$ alkoxy, a substituted or unsubstituted $C_1$-$C_6$ alkylcarbonyloxy, or a substituted or unsubstituted $C_6$-$C_{18}$ arylcarbonyloxy;
- n is 1;
- $R^3$ and $R^4$ are each independently hydrogen, hydroxyl, a substituted or unsubstituted $C_1$-$C_6$ alkoxy, a substituted or unsubstituted $C_1$-$C_6$ alkylcarbonyloxy, or a substituted or unsubstituted $C_6$-$C_{18}$ arylcarbonyloxy, or
- $R^3$ and $R^4$ together form —O—$CR^5R^6$—O—; wherein:
- $R^5$ and $R^6$ are each independently hydrogen, a substituted or unsubstituted $C_1$-$C_6$ alkyl, a substituted or unsubstituted $C_2$-$C_6$ alkenyl, a substituted or unsubstituted $C_2$-$C_6$ alkynyl, a substituted or unsubstituted $C_3$-$C_6$ cycloalkyl, a substituted or unsubstituted $C_3$-$C_6$ cycloalkenyl, a substituted or unsubstituted $C_3$-$C_6$ cycloalkynyl, a substituted or unsubstituted 3 to 6-membered heterocycloalkyl, a substituted or unsubstituted $C_6$-$C_{18}$ aryl, a substituted or unsubstituted $C_7$-$C_{20}$ arylalkyl, a substituted or unsubstituted 5 to 15-membered heteroaryl, or a substituted or unsubstituted 5 to 15-membered heteroaryl-$C_1$-$C_6$ alkyl;
- provided that at least one of $R^2$, $R^3$, $R^4$, $R^5$, and $R^6$ is a substituted or unsubstituted $C_6$-$C_{18}$ aryl, a substituted or unsubstituted $C_7$-$C_{20}$ arylalkyl, or a substituted or unsubstituted $C_6$-$C_{18}$ arylcarbonyloxy, and the remaining groups out of $R^2$, $R^3$, $R^4$, $R^5$, and $R^6$ are groups defined above; and
- in the case where the groups are substituted, the substituents are each independently at least one monovalent group or divalent group selected from the group consisting of a halogen (fluorine, chlorine, bromine or iodine), cyano, nitro, hydroxyl, a substituted or unsubstituted $C_1$-$C_6$ alkyl, a substituted or unsubstituted $C_2$-$C_6$ alkenyl, a substituted or unsubstituted $C_2$-$C_6$ alkynyl, a substituted or unsubstituted $C_3$-$C_6$ cycloalkyl, a substituted or unsubstituted $C_4$-$C_6$ cycloalkenyl, a substituted or unsubstituted $C_4$-$C_6$ cycloalkynyl, a substituted or unsubstituted 3 to 6-membered heterocycloalkyl, a substituted or unsubstituted $C_7$-$C_{11}$ cycloalkylalkyl, a substituted or unsubstituted 3 to 6-membered heterocycloalkyl-$C_1$-$C_6$ alkyl, a substituted or unsubstituted $C_6$-$C_{18}$ aryl, a substituted or unsubstituted $C_7$-$C_{20}$ arylalkyl, a substituted or unsubstituted 5 to 15-membered heteroaryl, a substituted or unsubstituted 5 to 15-membered heteroaryl-$C_1$-$C_6$ alkyl, a substituted or unsubstituted $C_1$-$C_6$ alkoxy, a substituted or unsubstituted $C_3$-$C_6$ cycloalkoxy, a substituted or unsubstituted 3 to 6-membered heterocycloalkoxy, a substituted or unsubstituted $C_6$-$C_{18}$ aryloxy, a substituted or unsubstituted $C_7$-$C_{20}$ arylalkyloxy, a substituted or unsubstituted 5 to 15-membered heteroaryloxy, a substituted or unsubstituted 5 to 15-membered heteroaryl-$C_1$-$C_6$ alkyloxy, a substituted or unsubstituted $C_1$-$C_6$ alkoxycarbonyl, a substituted or unsubstituted $C_3$-$C_6$ cycloalkoxycarbonyl, a substituted or unsubstituted $C_1$-$C_{20}$ acyl, a substituted or unsubstituted $C_1$-$C_{20}$ acyloxy, a substituted or unsubstituted amino, and oxo (C═O). In the case where the monovalent group is substituted, the substituent is preferably further selected from the monovalent groups or divalent groups described above, more preferably further selected from the unsubstituted monovalent groups or divalent groups described above.

According to one specific embodiment, further preferably, the compound represented by formula (I) is a compound, wherein:

- $R^1$ is a substituted or unsubstituted 5 to 15-membered heteroaryl;
- $R^2$ is a substituted or unsubstituted $C_1$-$C_6$ alkylcarbonyloxy, or a substituted or unsubstituted $C_6$-$C_{18}$ arylcarbonyloxy;
- n is 1;
- $R^3$ and $R^4$ are each independently a substituted or unsubstituted $C_1$-$C_6$ alkylcarbonyloxy, or a substituted or unsubstituted $C_6$-$C_{18}$ arylcarbonyloxy, or
- $R^3$ and $R^4$ together form —O—$CR^5R^6$—O—; wherein:
- $R^5$ and $R^6$ are each independently hydrogen, or a substituted or unsubstituted $C_6$-$C_{18}$ aryl;
- provided that at least one of $R^2$, $R^3$, $R^4$, $R^5$, and $R^6$ is a substituted or unsubstituted $C_6$-$C_{18}$ aryl, or a substituted or unsubstituted $C_6$-$C_{18}$ arylcarbonyloxy, and the remaining groups out of $R^2$, $R^3$, $R^4$, $R^5$, and $R^6$ are groups defined above; and
- in the case where the groups are substituted, the substituents are each independently at least one monovalent group or divalent group selected from the group consisting of a halogen (fluorine, chlorine, bromine or iodine), cyano, nitro, hydroxyl, a substituted or unsubstituted $C_1$-$C_6$ alkyl, a substituted or unsubstituted $C_2$-$C_6$ alkenyl, a substituted or unsubstituted $C_2$-$C_6$ alkynyl, a substituted or unsubstituted $C_3$-$C_6$ cycloalkyl, a substituted or unsubstituted $C_4$-$C_6$ cycloalkenyl, a substituted or unsubstituted $C_4$-$C_6$ cycloalkynyl, a substituted or unsubstituted 3 to 6-membered heterocycloalkyl, a substituted or unsubstituted $C_7$-$C_{11}$ cycloalkylalkyl, a substituted or unsubstituted 3 to 6-membered heterocycloalkyl-$C_1$-$C_6$ alkyl, a substituted or unsubstituted $C_6$-$C_{18}$ aryl, a substituted or unsubstituted $C_7$-$C_{20}$ arylalkyl, a substituted or unsubstituted 5 to 15-membered heteroaryl, a substituted or unsubstituted 5 to 15-membered heteroaryl-$C_1$-$C_6$ alkyl, a substituted or unsubstituted $C_1$-$C_6$ alkoxy, a substituted or unsubstituted $C_3$-$C_6$ cycloalkoxy, a substituted or unsubstituted 3 to 6-membered heterocycloalkoxy, a substituted or unsubstituted $C_6$-$C_{18}$ aryloxy, a substituted or unsubstituted $C_7$-$C_{20}$ arylalkyloxy, a substituted or unsubstituted 5 to 15-membered heteroaryloxy, a substituted or unsubstituted 5 to 15-membered heteroaryl-$C_1$-$C_6$ alkyloxy, a substituted or unsubstituted $C_1$-$C_6$ alkoxycarbonyl, a substituted or unsubstituted $C_3$-$C_6$ cycloalkoxycarbonyl, a substituted or unsubstituted $C_1$-$C_{20}$ acyl, a substituted or unsubstituted $C_1$-$C_{20}$ acyloxy, a substituted or unsubstituted amino, and oxo (C═O). In the case where the monovalent group is substituted, the substituent is preferably further selected from the monovalent groups or divalent groups described above, more preferably further selected from the unsubstituted monovalent groups or divalent groups described above.

Particularly preferably, the compound represented by formula (I) is a compound, wherein:

$R^4$ is pyridine-3-yl;

$R^2$ is acetoxy or 4-cyanobenzoyloxy;

n is 1;

$R^3$ and $R^4$ are both acetoxy or together form —O—$CR^5R^6$—O—; wherein:

$R^5$ is hydrogen; and $R^6$ is 2-methylphenyl.

Particularly preferably, the compound represented by formula (I) is one of the following compounds:

1,11-O-o-methylbenzylidene-7-O-p-cyanobenzoyl-1,7,11-trideacetyl pyripyropene A (PRD125, Japanese Patent No. 5592482);

7-p-cyanobenzoyl-7-deacetyl pyripyropene A (PRD017, Japanese Patent No. 5479110); and 7-O-p-cyanobenzoyl-1,11-di(O-isobutyryl)-1,7,11-trideacetyl pyripyropene A (PRD056, Japanese Patent No. 5479110); and other known pyripyropene derivatives (e.g., a compound disclosed in Ohshiro T. et. al, J. Antibiot. Vol. 61, p. 503-508 (2008); Owtawa M. et. al, Bioorg. Med. Chem. Lett. Vol. 23, p. 1285-1287 (2013); Owtawa M. et. al, Bioorg. Med. Chem. Lett. Vol. 23, p. 2659-2662 (2013); or Owtawa M. et. al, Bioorg. Med. Chem. Lett. Vol. 23, p. 3798-3801 (2013)). In the case where the compound represented by formula (I), which is the active component of the PCSK9 inhibitor of this aspect, is such a compound described above, the compound can exert particularly high inhibitory activity on the functions of PCSK9.

The compound represented by formula (I), which is the active component of the PCSK9 inhibitor of this aspect, may be purchased as a commercially available product or may be prepared based on a method according to a known literature.

The compound represented by formula (I) of this aspect, which is the active component of the PCSK9 inhibitor, may include not only the compound itself but also a salt thereof. The salt of the compound represented by formula (I) may be preferably, but is not limited to, salts with cations such as sodium ions, potassium ions, calcium ions, magnesium ions, or substituted or unsubstituted ammonium ions, or salts with inorganic acids such as hydrochloric acid, hydrobromic acid, sulfuric acid, nitrate, carbonic acid or phosphoric acid, or salts with organic acid anions such as formic acid, acetic acid, maleic acid, fumaric acid, benzoic acid, ascorbic acid, succinic acid, bismethylene salicylic acid, methanesulfonic acid, ethanedisulfonic acid, propionic acid, tartaric acid, salicylic acid, citric acid, gluconic acid, aspartic acid, stearic acid, palmitic acid, itaconic acid, glycolic acid, p-aminobenzoic acid, glutamic acid, benzenesulfonic acid, cyclohexylsulfamic acid, methanesulfonic acid, ethanesulfonic acid, isethionic acid, p-toluenesulfonic acid, or naphthalenesulfonic acid. Even in the form of a salt described above, the compound represented by formula (I) can exert high inhibitory activity on the functions of PCSK9.

The compound represented by formula (I), which is the active component of the PCSK9 inhibitor of this aspect, may include not only the compound itself but also a solvate of the compound or a salt thereof. A solvent that can form the solvate of the compound or a salt thereof may be preferably, but not limited to, water or an organic solvent such as lower alcohols (e.g., alcohols having 1 to 6 carbon atoms such as methanol, ethanol, or 2-propanol (isopropyl alcohol)), higher alcohols (e.g., alcohols having 7 or more carbon atoms such as 1-heptanol or 1-octanol), dimethylsulfoxide (DMSO), acetic acid, ethanolamine, or ethyl acetate. Even in the form of a solvate with the solvent described above, the compound represented by formula (I) or a salt thereof can exert high inhibitory activity on the functions of PCSK9.

The compound represented by formula (I), which is the active component of the PCSK9 inhibitor of this aspect, may include not only the compound itself but also its protected form. In this description, the "protected form" means a form in which a protecting group is introduced into one or a plurality of functional groups (e.g., an amino group, a hydroxyl group, or a carboxylic acid group). In this description, the protected form of the compound represented by each formula may be referred to as a protective derivative of the compound represented by each formula. In this description, the "protecting group" means a group which is introduced into a specific functional group for stopping process of an undesirable reaction, is quantitatively removed under specific reaction conditions and is substantially stable, that is, reaction-inactive under other reaction conditions. The protecting group that can form the protected form of the compound may be preferably, but not limited to, t-butoxycarbonyl (Boc), 2-bromobenzyloxycarbonyl (BrZ), or 9-fluorenylmethoxycarbonyl (Fmoc) for the protecting group of an amino group, a silyl (e.g., t-butyldimethylsilyl (TBS), triisopropyl silyl (TIPS), or tert-butyldiphenylsilyl (TBDPS)) or an alkoxy (e.g., methoxymethoxy (MOM) or methoxy (Me)) for the protecting group of a hydroxyl group, an alkyl ester (e.g., methyl, ethyl or isopropyl ester), an arylalkyl ester (e.g., benzyl ester), or an amide (e.g., amides with oxazolidinones), in the case of the protecting group of a carboxylic acid group, respectively. Protection and deprotection with the protecting group can be appropriately carried out by those skilled in the art based on the known reaction conditions. Even in the case of the protected form with the protecting group described above of the compound represented by formula (I), the compound may be used without substantially reducing the inhibitory activity on the functions of PCSK9.

In the case where the compound represented by formula (I), which is the active component of the PCSK9 inhibitor of this aspect, has one or more tautomers, the compound may also include the form of individual tautomers of the compound.

Further, in the case where the compound represented by formula (I), which is the active component of the PCSK9 inhibitor of this aspect, has one or a plurality of stereocenters (chiral centers), the compound may also include individual enantiomers and diastereomers of the compound, and mixtures thereof such as racemates.

The compound represented by formula (I), which is the active component of the PCSK9 inhibitor of this aspect, can exert high inhibitory activity on the functions of PCSK9 by having the aforementioned characteristics.

<2. Pharmaceutical Use>

The compound represented by formula (I) that is an active component of the PCSK9 inhibitor of one aspect of the present disclosure has high inhibitory activity on the functions of PCSK9. When the compound represented by formula (I) is administered to a subject, specific symptoms, diseases, or disorders of the subject can be prevented or treated through the PCSK9 inhibitory activity. Therefore, another aspect of the present disclosure relates to a medicament or a pharmaceutical composition containing the PCSK9 inhibitor of one aspect of the present disclosure or the compound represented by formula (I) that is the active component of the PCSK9 inhibitor, a pharmaceutically acceptable salt thereof, or a pharmaceutically acceptable solvate thereof, as an active component.

In each aspect of the present disclosure, "PCSK9 inhibition" and "PCSK9 inhibitory activity" mean an inhibition to the functions of PCSK9 and the inhibitory activity on the functions of PCSK9.

The PCSK9 inhibitory activity of the compound represented by formula (I) can be determined, but not limited to, by adding the compound represented by formula (I) to cells derived from human or non-human mammals (e.g., warm-blooded animals such as pigs, dogs, bovines, rats, mice, guinea pigs, rabbits, chickens, sheep, cats, monkeys, sacred baboons, or chimpanzees) (e.g., HepG2 cells derived from human liver cancer), culturing the cells under predetermined conditions, then measuring the amount of PCSK9 produced in the culture medium and/or the cells, and comparing it with the amount produced in the control without addition of the compound. Alternatively, the PCSK9 inhibitory activity of the compound represented by formula (I) can be determined by administering the compound to the human or non-human mammals described above under predetermined conditions, then measuring the amount of PCSK9 produced and/or the amount of neutral lipids produced in the blood and/or organs (e.g., the liver), and comparing it with the amount produced in the control without addition of the compound.

The compound represented by formula (I) can exert PCSK9 inhibitory activity generally at a concentration of 1.0 micro gram/mL or more, particularly at a concentration of 10 micro gram/mL or more. In the case where the compound is used at a concentration in the aforementioned range, the compound represented by formula (I) can exert high inhibitory activity on PCSK9.

In the case where the compound represented by formula (I) is applied to a pharmaceutical use, the compound represented by formula (I) may include not only the compound itself but also a pharmaceutically acceptable salt of the compound, and a pharmaceutically acceptable solvate thereof. The pharmaceutically acceptable salt of the compound represented by formula (I) and the pharmaceutically acceptable solvate thereof are preferably, but not limited to, the salts or solvates described above. In the case where the compound represented by formula (I) is in the form of a pharmaceutically acceptable salt or a pharmaceutically acceptable solvate, the compound can be applied to a desired pharmaceutical use without substantially reducing the PCSK9 inhibitory activity.

In the case where the compound represented by formula (I) is applied to a pharmaceutical use, the compound represented by formula (I) may include not only the compound itself but also the prodrug form of the compound. In this description, the "prodrug" means a compound that is converted to a parent drug in vivo. Examples of the prodrug form of the compound can include, but not limited to, for example, in the presence of a hydroxyl group, an ester of the hydroxyl group and any carboxylic acid, and an amide of the hydroxyl group and any amine; and, in the presence of the amino group, an amide of an amino group and any carboxylic acid. In the case where the compound represented by formula (I) is in the prodrug form, the pharmacokinetics upon administration of the prodrug form to the subject can be improved, without substantially reducing the PCSK9 inhibitory activity of the compound represented by formula (I) that is the parent drug.

In the case where the compound represented by formula (I) is applied to a pharmaceutical use, the compound may be used alone or in combination with one or more pharmaceutically acceptable ingredients. The medicament of this aspect can be formulated into various dosage forms commonly used in the art, depending on the desired mode of administration. Therefore, the medicament of this aspect can be provided further in the form of a pharmaceutical composition containing the PCSK9 inhibitor of one aspect of the present disclosure or the compound represented by formula (I) that is the active component of the PCSK9 inhibitor, a pharmaceutically acceptable salt thereof, or a pharmaceutically acceptable solvate thereof, and one or more pharmaceutically acceptable carriers. The pharmaceutical composition of this aspect may contain one or more pharmaceutically acceptable media (e.g., solvents such as sterile water or solutions such as saline), excipients, binders, vehicles, solubilizers, preservatives, stabilizers, swelling agents, lubricants, surfactants, emulsifiers, oily liquids (e.g., vegetable oils), suspending agents, buffers, analgesic agents, antioxidants, sweeteners, and flavoring agents, in addition to the ingredients.

The dosage form of the medicament of this aspect containing the PCSK9 inhibitor of one aspect of the present disclosure or the compound represented by formula (I) that is the active component of the PCSK9 inhibitor, a pharmaceutically acceptable salt thereof, or a pharmaceutically acceptable solvate thereof, as an ingredient is not specifically limited and may be a preparation for use in parenteral administration or a preparation for use in oral administration. Further, the dosage form of the medicament of this aspect may be a preparation in the unit-dosage form or a preparation in the multi-dosage form. Examples of the preparation for use in parenteral administration can include injections such as sterile solutions or suspensions with water or other pharmaceutically acceptable media. Examples of ingredients that can be mixed with injections can include, but not limited to, vehicles such as isotonic solutions containing physiological saline, glucose or other adjuvants (e.g., D-sorbitol, D-mannitol, D-mannose, or sodium chloride), solubilizers such as alcohols (e.g., ethanol or benzyl alcohol), polyalcohols (e.g., propylene glycol or polyethylene glycol), or esters (e.g., benzyl benzoate), nonionic surfactants such as polysorbate 80 (trademark) or polyoxyethylene hardened castor oil, oily liquids such as sesame oil or soybean oil, buffers such as phosphate buffer or sodium acetate buffer, analgesic agents such as benzalkonium chloride or procaine hydrochloride, stabilizers such as human serum albumin or polyethylene glycol, preservatives, and antioxidants. The injections prepared are usually filled in suitable vials (e.g., ampoules) and stored in a suitable environment until use.

Examples of the preparation for use in oral administration can include tablets, pills, powders, capsules, soft capsules, microcapsule agents, elixirs, liquid formulations, syrups, slurry agents, and suspensions. The tablets may be formulated into dosage forms of sugar-coated or soluble-coated tablets, gelatin encapsulated tablets, enteric-coated tablets, orally disintegrating tablets (OD tablets), or film-coated tablets or may be formulated into dosage forms of bi-layered tablets or multilayered tablets, if desired.

Examples of the ingredients that can be mixed in the tablets or capsules can include, but not limited to, binders such as water, ethanol, propanol, simple syrup, glucose solution, carboxymethylcellulose, shellac, methylcellulose, potassium phosphate, polyvinylpyrrolidone, gelatin, corn starch, tragacanth gum, or gum arabic; excipients such as crystalline cellulose, lactose, white sugar, sodium chloride, glucose, urea, starch, calcium carbonate, kaolin, or silicic acid; disintegrants such as dried starch, sodium alginate, powdered agar, laminaran powder, sodium bicarbonate, calcium carbonate, polyoxyethylene sorbitan fatty acid ester, sodium lauryl sulfate, stearic acid monoglyceride, starch, or lactose; disintegration inhibitors such as white sugar, stearic cacao butter, or hydrogenated oil; absorption enhancers such as quaternary ammonium salt or sodium lauryl sulfate; humectants such as glycerin or starch; adsorbents such as starch, lactose, kaolin, bentonite, or colloidal silicic acid; lubricants such as refined talc, stearate (e.g., magnesium stearate), boric acid powder, or polyethylene glycol; sweeteners such as sucrose, lactose, or saccharin; and flavoring agents such as peppermint, gaultheria adenothrix (akamono) oil, or cherry. In the case of a capsule, the preparation may further contain a liquid carrier such as fats and oils.

The medicament of this aspect containing the PCSK9 inhibitor of one aspect of the present disclosure or the compound represented by formula (I) that is the active component of the PCSK9 inhibitor, a pharmaceutically acceptable salt thereof, or a pharmaceutically acceptable solvate thereof, as an active component, can be formulated as a depot preparation. In this case, the medicament of this aspect in the dosage form of the depot preparation can be administered, for example, subcutaneously or intramuscularly, or by intramuscular injection. The PCSK9 inhibitory activity of the compound represented by formula (I) can be continuously exerted over a long period of time when the medicament of this aspect is applied by the depot preparation.

The medicament of this aspect containing the PCSK9 inhibitor of one aspect of the present disclosure or the compound represented by formula (I) that is the active component of the PCSK9 inhibitor, a pharmaceutically acceptable salt thereof, or a pharmaceutically acceptable solvate thereof, as an active component, can be used in combination with one or more additional agents that are useful as medicaments. Examples of the additional agents to be used in combination can include, but not limited to, statin drugs (e.g., atorvastatin), pyripyropene A, and analogs or derivatives thereof, and ezetimibe. In this case, the medicament of this aspect may be formed as a combined drug containing the PCSK9 inhibitor of one aspect of the present disclosure or the compound represented by formula (I) that is the active component of the PCSK9 inhibitor, a pharmaceutically acceptable salt thereof, or a pharmaceutically acceptable solvate thereof with one or more additional agents. The combined drug may be in the form of a pharmaceutical composition comprising the PCSK9 inhibitor of one aspect of the present disclosure or the compound represented by formula (I) that is formulated by combining the active component of the PCSK9 inhibitor, a pharmaceutically acceptable salt thereof, or a pharmaceutically acceptable solvate thereof, with one or more additional agents, or may be in the form of a pharmaceutical composition containing the PCSK9 inhibitor of one aspect of the present disclosure or the compound represented by formula (I) that is the active component of the PCSK9 inhibitor, a pharmaceutically acceptable salt thereof, or a pharmaceutically acceptable solvate thereof to be used in combination with one or more additional agents. In the form of the combined drug, the drug of this aspect may be provided in the form of a single preparation containing the PCSK9 inhibitor of one aspect of the present disclosure or the compound represented by formula (I) that is the active component of the PCSK9 inhibitor, a pharmaceutically acceptable salt thereof, or a pharmaceutically acceptable solvate thereof with one or more drugs, or may be provided in the form of a pharmaceutical combination or a kit containing a plurality of preparations formulated separately from the one or more drugs. In the form of the pharmaceutical combination or the kit, the preparations may be administered simultaneously or separately (e.g., serially).

The medicament of this aspect containing the PCSK9 inhibitor of one aspect of the present disclosure or the compound represented by formula (I) that is the active component of the PCSK9 inhibitor, a pharmaceutically acceptable salt thereof, or a pharmaceutically acceptable solvate thereof, as an active component, can prevent or treat various symptoms, diseases, and/or disorders related to the functions of PCSK9, in the same manner. Examples of the symptoms, diseases, and/or disorders can include, but not limited to, hypercholesterolemia, familial hypersterolemia, hyperlipidemia, arteriosclerosis, fatty liver, adiposity, pancreatic beta cell failure, cholesteryl ester accumulation, Wolman's disease, Niemann Pick's disease type C, symptoms in the survivors of Hodgkin's lymphangioma, Tangier disease, Kawasaki's disease, sitosterolemia, juvenile idiopathic arthritis, familial hypercholesterolemia, diabetes (e.g., type-1 diabetes and type-2 diabetes), symptoms in kidney transplant patients, and symptoms in heart transplant patients, which are all related to the functions of PCSK9. The application of the medicament of this aspect containing the PCSK9 inhibitor of one aspect of the present disclosure or the compound represented by formula (I) that is the active component of the PCSK9 inhibitor, a pharmaceutically acceptable salt thereof, or a pharmaceutically acceptable solvate thereof, as an active component, can also be beneficial to prevent or treat of the symptoms, diseases, and/or disorders, as will be appreciated by those skilled in the art, that are generally manageable (preventable or treatable) through use of anti-PSCK9 antibodies. The symptoms, diseases, and/or disorders are preferably one or more symptoms, diseases, or disorders selected from the group consisting of hypercholesterolemia, familial hypersterolemia, hyperlipidemia, arteriosclerosis, fatty liver, adiposity, pancreatic beta cell failure, cholesteryl ester accumulation, Wolman's disease, Niemann Pick's disease type C, symptoms in the survivors of Hodgkin's lymphangioma, Tangier disease, Kawasaki's disease, sitosterolemia, juvenile idiopathic arthritis, familial hypercholesterolemia, diabetes (e.g., type-1 diabetes and type-2 diabetes), symptoms in kidney transplant patients, and symptoms in heart transplant patients, which are all related to the functions of PCSK9. The fatty liver may include non-alcoholic steatohepatitis (NASH) or non-alcoholic fatty liver disease (NAFLD). The arteriosclerosis may include atherosclerosis. The medicament of this aspect can be administered to a subject in need of the prevention or treatment of diseases, symptoms, or disorders related to the functions of PCSK9 to prevent or treat the diseases, symptoms, or disorders.

In each aspect of the present disclosure, the phrase "symptoms, diseases, and/or disorders related to the functions of PCSK9" mean symptoms, diseases, and/or disorders caused by suppression and/or deficiency of exhibition of the PCSK9 functions. The relations between the symptoms, diseases, and/or disorders and the functions of PCSK9 can be specified, but not limited to, for example, by confirming suppression and/or deficiency of exhibition of the PCSK9 functions in a subject suffering from the symptoms, diseases, and/or disorders or by confirming that, after administration of at least one agent selected from the group consisting of HMG-CoA reductase inhibitors such as statin drugs (e.g., atorvastatin), and SOAT2 inhibitors other than pyripyropene A and analogs or derivatives thereof to a subject suffering from the symptoms, diseases, and/or disorders, the effect of the agent is insufficient.

The medicament of this aspect containing the PCSK9 inhibitor of one aspect of the present disclosure or the compound represented by formula (I) that is the active component of the PCSK9 inhibitor, a pharmaceutically acceptable salt thereof, or a pharmaceutically acceptable solvate thereof, as an active component, can be applied to various subjects in need of prevention or treatment of the symptoms, diseases, and/or disorders, which are related to the functions of PCSK9. The subjects are preferably test subjects or patients of human or non-human mammals (e.g., warm-blooded animals such as pigs, dogs, bovines, rats, mice, guinea pigs, rabbits, chickens, sheep, cats, monkeys, sacred baboons, or chimpanzees). The medicament of this aspect can be administered to the subject to prevent or treat various symptoms, diseases, and/or disorders related to the functions of PCSK9 in the subject.

In this description, the "prevention" means to substantially prevent generation (onset or expression) of the symptoms, diseases, and/or disorders. In this description, the "treatment" means to suppress (e.g., suppress the progression), ameliorate, recover, and/or cure from the symptoms, diseases, and/or disorders that have generated (onset or expressed).

The PCSK9 inhibitor of one aspect of the present disclosure, and the compound represented by formula (I) that is the active component of the PCSK9 inhibitor can be used in prevention or treatment of the symptoms, diseases, and/or disorders described above, which are related to the functions of PCSK9 (e.g., hypercholesterolemia, familial hypersterolemia, hyperlipidemia, arteriosclerosis (e.g., atherosclerosis), fatty liver (e.g., NASH or NAFLD), adiposity, pancreatic beta cell failure, cholesteryl ester accumulation, Wolman's disease, Niemann Pick's disease type C, symptoms in the survivors of Hodgkin's lymphangioma, Tangier disease, Kawasaki's disease, sitosterolemia, juvenile idiopathic arthritis, familial hypercholesterolemia, diabetes (e.g., type-1 diabetes and type-2 diabetes), symptoms in kidney transplant patients or symptoms in heart transplant patients) in a subject suffering from the symptoms, diseases, and/or disorders. Therefore, the medicament of this aspect is preferably a medicament for use in prevention or treatment of the symptoms, diseases, and/or disorders described above, related to the functions of PCSK9, more preferably a medicament for use in prevention or treatment of one or more symptoms, diseases, and/or disorders selected from the group consisting of hypercholesterolemia, familial hypersterolemia, hyperlipidemia, arteriosclerosis (e.g., atherosclerosis), fatty liver (e.g., NASH or NAFLD), adiposity, pancreatic beta cell failure, cholesteryl ester accumulation, Wolman's disease, Niemann Pick's disease type C, symptoms in the survivors of Hodgkin's lymphangioma, Tangier disease, Kawasaki's disease, sitosterolemia, juvenile idiopathic arthritis, familial hypercholesterolemia, diabetes (e.g., type-1 diabetes and type-2 diabetes), symptoms in kidney transplant patients, and symptoms in heart transplant patients, which are related to the functions of PCSK9. Use of the medicament of this aspect for preventing or treating the symptoms, diseases, and/or disorders, which are related to the functions of PCSK9 enables the symptoms, diseases, and/or disorders, which are related to the functions of PCSK9 to be prevented or treated through the PCSK9 inhibitory activity of the compound represented by formula (I).

The PCSK9 inhibitor of one aspect of the present disclosure, and the compound represented by formula (I) that is the active component of the PCSK9 inhibitor can be used in prevention or treatment of the symptoms, diseases, and/or disorders in a subject suffering from symptoms, diseases, and/or disorders described above, which are related to the functions of PCSK9 (e.g., hypercholesterolemia, familial hypersterolemia, hyperlipidemia, arteriosclerosis (e.g., atherosclerosis), fatty liver (e.g., NASH or NAFLD), adiposity, pancreatic beta cell failure, cholesteryl ester accumulation, Wolman's disease, Niemann Pick's disease type C, symptoms in the survivors of Hodgkin's lymphangioma, Tangier disease, Kawasaki's disease, sitosterolemia, juvenile idiopathic arthritis, familial hypercholesterolemia, diabetes (e.g., type-1 diabetes and type-2 diabetes), symptoms in kidney transplant patients or symptoms in heart transplant patients). Therefore, another aspect of the present disclosure is a method for preventing or treating the symptoms, diseases, and/or disorders, which are related to the functions of PCSK9, comprising administering an effective amount of the PCSK9 inhibitor of one aspect of the present disclosure or the compound represented by formula (I) that is the active component of the PCSK9 inhibitor, a pharmaceutically acceptable salt thereof, or a pharmaceutically acceptable solvate thereof to a subject in need of prevention or treatment of the symptoms, diseases, and/or disorders, described above. The symptoms, diseases, and/or disorders are preferably one or more symptoms, diseases, and/or disorders, which are related to the functions of PCSK9, selected from the group consisting of hypercholesterolemia, familial hypersterolemia, hyperlipidemia, arteriosclerosis (e.g., atherosclerosis), fatty liver (e.g., NASH or NAFLD) adiposity, pancreatic beta cell failure, cholesteryl ester accumulation, Wolman's disease, Niemann Pick's disease type C, symptoms in the survivors of Hodgkin's lymphangioma, Tangier disease, Kawasaki's disease, sitosterolemia, juvenile idiopathic arthritis, familial hypercholesterolemia, diabetes (e.g., type-1 diabetes and type-2 diabetes), symptoms in kidney transplant patients, and symptoms in heart transplant patients. The PCSK9 inhibitor of one aspect of the present disclosure or the compound represented by formula (I) that is the active component of the PCSK9 inhibitor can be administered to a subject in need of prevention or treatment of the symptoms, diseases, and/or disorders, which are related to the functions of PCSK9 to prevent or treat the symptoms, diseases, and/or disorders, which are related to the functions of PCSK9 through the PCSK9 inhibitory activity of the compound represented by formula (I).

Another aspect of the present disclosure is the PCSK9 inhibitor of one aspect of the present disclosure or the compound represented by formula (I) that is the active component of the PCSK9 inhibitor, a pharmaceutically acceptable salt thereof, or a pharmaceutically acceptable solvate thereof, for use in prevention or treatment of the symptoms, diseases, and/or disorders, which are related to the functions of PCSK9, described above (e.g., hypercholesterolemia, familial hypersterolemia, hyperlipidemia, arteriosclerosis (e.g., atherosclerosis), fatty liver (e.g., NASH or NAFLD), adiposity, pancreatic beta cell failure, cholesteryl ester accumulation, Wolman's disease, Niemann Pick's disease type C, symptoms in the survivors of Hodgkin's lymphangioma, Tangier disease, Kawasaki's disease, sitosterolemia, juvenile idiopathic arthritis, familial hypercholesterolemia, diabetes (e.g., type-1 diabetes and type-2 diabetes), symptoms in kidney transplant patients or symptoms in heart transplant patients). Another aspect of the present disclosure is use of the PCSK9 inhibitor of one aspect of the present disclosure or the compound represented by formula (I) that is the active component of the PCSK9 inhibitor, a pharmaceutically acceptable salt thereof, or a pharmaceutically acceptable solvate thereof in production of a medicament for prevention or treatment of the symptoms, diseases, and/or disorders, which are related to the functions of PCSK9, described above (e.g., hypercholesterolemia, familial hypersterolemia, hyperlipidemia, arteriosclerosis (e.g., atherosclerosis), fatty liver (e.g., NASH or NAFLD), adiposity, pancreatic beta cell failure, cholesteryl ester accumulation, Wolman's disease, Niemann Pick's disease type C, symptoms in the survivors of Hodgkin's lymphangioma, Tangier disease, Kawasaki's disease, sitosterolemia, juvenile idiopathic arthritis, familial hypercholesterolemia, diabetes (e.g., type-1 diabetes and type-2 diabetes), symptoms in kidney transplant patients or symptoms in heart transplant patients). Another aspect of the present disclosure is use of the PCSK9 inhibitor of one aspect of the present disclosure or the compound represented by formula (I) that is the active component of the PCSK9 inhibitor, a pharmaceutically acceptable salt thereof, or a pharmaceutically acceptable solvate thereof for prevention or treatment of the symptoms, diseases, and/or disorders, which are related to the functions of PCSK9, described above (e.g., hypercholesterolemia, familial hypersterolemia, hyperlipidemia, arteriosclerosis (e.g., atherosclerosis), fatty liver (e.g., NASH or NAFLD), adiposity, pancreatic beta cell failure, cholesteryl ester accumulation, Wolman's disease, Niemann Pick's disease type C, symptoms in the survivors of Hodgkin's lymphangioma, Tangier disease, Kawasaki's disease, sitosterolemia, juvenile idiopathic arthritis, familial hypercholesterolemia, diabetes (e.g., type-1 diabetes and type-2 diabetes), symptoms in kidney transplant patients or symptoms in heart transplant patients). The symptoms, diseases, and/or disorders are preferably one or more symptoms, diseases, and/or disorders, which are related to the functions of PCSK9, selected from the group consisting of hypercholesterolemia, familial hypersterolemia, hyperlipidemia, arteriosclerosis (e.g., atherosclerosis), fatty liver (e.g., NASH or NAFLD), adiposity, pancreatic beta cell failure, cholesteryl ester accumulation, Wolman's disease, Niemann Pick's disease type C, symptoms in the survivors of Hodgkin's lymphangioma, Tangier disease, Kawasaki's disease, sitosterolemia, juvenile idiopathic arthritis, familial hypercholesterolemia, diabetes (e.g., type-1 diabetes and type-2 diabetes), symptoms in kidney transplant patients, and symptoms in heart transplant patients. Use of the PCSK9 inhibitor of one aspect of the present disclosure or the compound represented by formula (I) that is the active component of the PCSK9 inhibitor for preventing or treating the symptoms, diseases, and/or disorders, which are related to the functions of PCSK9 can prevent or treat the symptoms, diseases, and/or disorders, which are related to the functions of PCSK9, through the PCSK9 inhibitory activity of the compound represented by formula (I).

In the case of administering the medicament of this aspect containing the PCSK9 inhibitor of one aspect of the present disclosure or the compound represented by formula (I) that is the active component of the PCSK9 inhibitor, a pharmaceutically acceptable salt thereof, or a pharmaceutically acceptable solvate thereof, as an active component, to a subject, particularly, a human patient, the exact dose and usage (e.g., the administration dose, administration frequency, and/or administration route) should be finally determined by the physician or doctor in charge, in consideration of the therapeutically effective dosage, administration frequency, and administration route, in view of many factors such as the age and gender of the subject, the exact state (e.g., severity) of the symptom, disease, and/or disorder to be prevented or treated, and the administration route. Therefore, in the medicament of this aspect, the PCSK9 inhibitor of one aspect of the present disclosure or the compound represented by formula (I) that is the active component of the PCSK9 inhibitor is administered to the subject in a therapeutically effective amount and administration frequency. For example, in the case of administering the medicament of this aspect to a human patient, the dosage of the compound represented by formula (I) is generally in the range of 0.001 to 100 mg/kg body weight per dose, typically in the range of 0.01 to 50 mg/kg body weight per dose, particularly in the range of 0.1 to 10 mg/kg body weight per dose. Further, the administration frequency of the medicament of this aspect can be, for example, once or more than once a day, or once every few days. Further, the administration route of the medicament of this aspect is not specifically limited, and it may be administered once or multiple times via oral route or parenteral route (e.g., intrarectally, transmucosaly, intestinally, intramuscularly, subcutaneously, intraosseously, intrathecally, intraventricularly, intravenously, intravitreallyy, intraperitoneally, intranasally, or intraocularly). Use of the medicament of this aspect in such a dose and usage can prevent or treat the symptoms, diseases, and/or disorders, which are related to the functions of PCSK9 through the PCSK9 inhibitory activity of the compound represented by formula (I).

EXAMPLES

Hereinafter, the present disclosure is further specifically described by way of examples. However, the technical scope of the present disclosure is not limited to these examples.

<I. Pharmacological Test of Compound>

[I-1: In Vitro PCSK9 Inhibition Test of Subject Compound]

HepG2 cells derived from human liver cancer ($5\times10^5$ cells/mL, 0.25 mL/well) were seeded on a 48-well plate. Subject compounds: 1,11-O-o-methylbenzylidene-7-O-p-cyanobenzoyl-1,7,11-trideacetyl pyripyropene A (PRD125), 7-p-cyanobenzoyl-7-deacetyl pyripyropene A (PRD017), 7-O-p-cyanobenzoyl-1,11-di(O-isobutyryl)-1,7,11-trideacetyl pyripyropene A (PRD056), and comparative compounds: pyripyropene A (PPPA) and a known statin drug, atorvastatin (Atr), were each added to the wells at a predetermined concentration, and the cells were cultured in a serum-free medium at 37° C. for 24 hours. As a control, the cells were treated in wells in the absense of compound under similar conditions. After culturing, the culture medium and the cells were collected. PCSK9 in the culture medium and the cells was detected by Western blotting. Using an image analysis software (ImageLab), band intensity of the detected PCSK9 was quantified. The quantitative value of each band intensity was corrected based on the quantitative value of the band intensity of glyceraldehyde-3-phosphate dehydrogenase (GAPDH) that is a loading control for Western blotting. The results of detecting PCSK9 and ProPCSK9 in the culture medium and the cells by Western blotting are shown in FIG. 1. In the figure, FIG. 1A indicates the results of detecting PCSK9 and ProPCSK9 in the culture medium and the cells with PRD017 or PRD056 added, and FIG. 1B indicates the results of detecting PCSK9 and ProPCSK9 in the culture medium and the cells with PRD125, Atr, or PPPA added. Further, the results of quantifying the PCSK9 band intensity detected by Western blotting are shown in FIGS. 2 and 3, and Table 1. In FIG. 2, FIG. 2A indicates the results with PRD017 added, FIG. 2B indicates the results with PRD056 added, and FIG. 2C indicates the results with PRD125 added, respectively. In FIG. 3, FIG. 3A indicates the results with Atr added, and FIG. 3B indicates the results with PPPA added, respectively. In the figures, the horizontal axis indicates the concentration of the compound (micro gram/mL) added, and the vertical axis indicates the total amount of PCSK9(%), respectively. The total amount of PCSK9 is a percentage with respect to the total amount of PCSK9 in the control. The values in Table 1 are percentages with respect to the total amount of PCSK9 in the control.

The chemical structures of the subject compounds (PRD125, PRD017, and PRD056) and the comparative compound (PPPA) are shown below. PRD125 was prepared based on the method described in Japanese Patent No. 5592482. PRD017 and PRD056 were prepared based on the method described in Japanese Patent No. 5479110.

[Formula 3]

PPPA

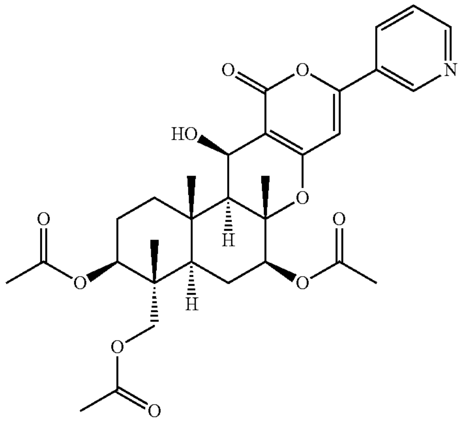

PRD125

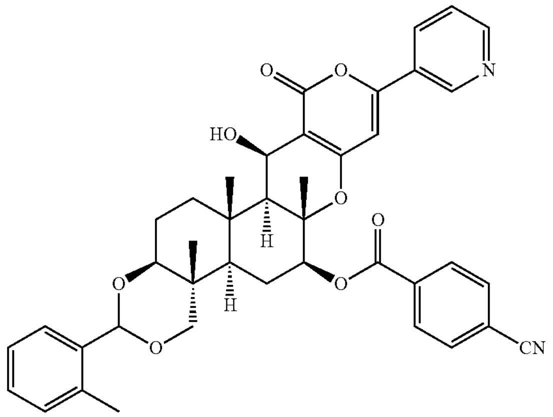

PRD017

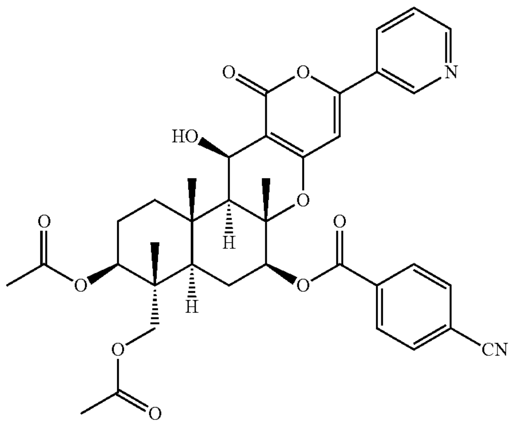

-continued

PRD056

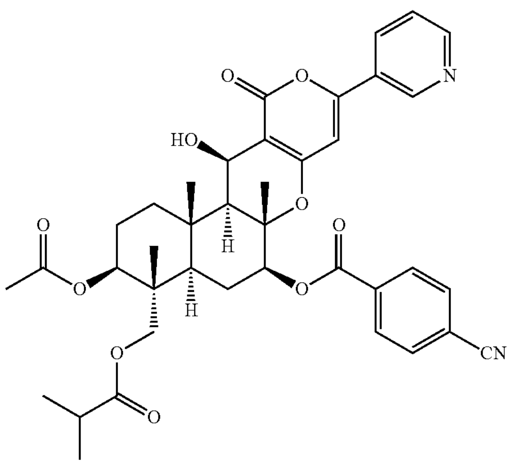

TABLE 1

| Additive compound | Control (without compound) | PPPA | | PRD017 | | PRD056 | |
|---|---|---|---|---|---|---|---|
| (micro gram/mL) | 0 | 1.0 | 10 | 1.0 | 10 | 1.0 | 10 |
| PCSK9 (in culture medium) | 49.7% | 45.2% | 31.7% | 28.3% | 22.0% | 21.1% | 15.2% |
| ProPCSK9 (in cells) | 14.3% | 35.7% | 19.7% | 11.7% | 6.6% | 8.1% | 6.4% |
| PCSK9 (in cells) | 36.0% | 35.7% | 38.4% | 40.3% | 29.4% | 27.2% | 34.5% |
| Total PCSK9 amount | 100% | 116.6% | 89.8% | 80.3% | 58.0% | 56.4% | 56.1% |

| Additive compound | PRD125 | | Atr | |
|---|---|---|---|---|
| (micro gram/mL) | 1.0 | 10 | 1.0 | 10 |
| PCSK9 (in culture medium) | 23.0% | 20.7% | 129.3% | 136.1% |
| ProPCSK9 (in cells) | 12.8% | 10.4% | 90.0% | 97.6% |
| PCSK9 (in cells) | 20.7% | 23.6% | 49.4% | 63.2% |
| Total PCSK9 amount | 56.5% | 54.7% | 268.7% | 296.8% |

As shown in FIG. 1 and Table 1, in the case where PPPA was added, no significant difference was observed in the amount of PCSK9 in the culture medium and the cells, as compared with the amount of PCSK9 in the control. In contrast, in the case where PRD017 was added, the total amount of PCSK9 decreased depending on the concentration added. For example, in the case where 10 micro gram/mL of PRD017 was added, the total amount of PCSK9 decreased to 58% of the total amount of PCSK9 in the control. In this case, the amount of PCSK9 in the culture medium decreased to 44% of the amount of PCSK9 in the culture medium of the control, and the amount of ProPCSK9 in the cells decreased to 46% of the amount of ProPCSK9 in the cells of the control, respectively. In the case where PRD056 was added, the total amount of PCSK9 decreased depending on the concentration added. For example, in the case where 10 micro gram/mL of PRD056 was added, the total amount of PCSK9 decreased to 56.1% of the total amount of PCSK9 in the control. In this case, the amount of PCSK9 in the culture medium decreased to 30% with respect to the amount of PCSK9 in the culture medium of the control, and the amount of ProPCSK9 in the cells decreased to 44.8% with respect to the amount of ProPCSK9 in the cells of the control, respectively. In the case where PRD125 was added, the total amount of PCSK9 decreased depending on the concentration added. For example, in the case where 10 micro gram/mL of PRD125 was added, the total amount of PCSK9 decreased to 54.7% with respect to the total amount of PCSK9 in the control. In this case, the amount of PCSK9 in the culture medium decreased to 41.6% with respect to the amount of PCSK9 in the culture medium of the control. In contrast, in the case where Atr was added, the amount of PCSK9 in the culture medium and the cells rather increased. For example, in the case where 10 micro gram/mL of Atr was added, the total amount of PCSK9 increased to 296.8% with respect to the total amount of PCSK9 in the control. In this case, the amount of PCSK9 in the culture medium increased to 273.8% with respect to the amount of PCSK9 in the culture medium of the control, and the amount of ProPCSK9 and the amount of PCSK9 in the cells increased to 682.5% and 175.6% with respect to the amount of ProPCSK9 and the amount of PCSK9 in the cells of the control, respectively.

[I-2: In-Vivo PCSK9 Inhibition Test of Subject Compounds]

Female and male mice (C57BL/6J) were fed with high-fat diet (HFD) for 4 weeks. The mice were grouped into the control group, the PPPA-administered group and PRD125-administered group (N=20 for males and N=20 for females in each group). The PPPA-administered group and the PRD125-administered group were fed with HFD with each subject compound or a comparative compound added for 8 weeks. The control group was fed only with HFD for 8 weeks. The PPPA was administered at a dose of 50 mg/kg body weight/day, and the PRD125 was administered at a dose of 10 mg/kg body weight/day, respectively. After the completion of the administration period, the blood was collected and the liver was extracted under anesthesia, from the mice of each group. The amount of LDL-cholesterol and the amount of PCSK9 in the blood, and the amount of total cholesterol, the amount of cholesteryl ester, and the amount of triglyceride in the liver were measured. The averages and the standard deviations of the measured values in each group were calculated. Further, the p values for the values of the PPPA-administered group and the PRD125-administered group with respect to the value of the control group were calculated by the student t-test. The amount of neutral lipids in the liver and blood are shown in FIG. 4. In the figure, FIG. 4A indicates the amount of total cholesterol in the liver, FIG. 4B indicates the amount of cholesteryl ester in the liver, FIG. 4C indicates the amount of triglyceride in the liver, and FIG. 4D indicates the amount of LDL-cholesterol in the blood, respectively. The symbol * indicates that each p value with respect to the value of the control group is 0.05 or less, the symbol  indicates that each p value with respect to the value of the control group is 0.01 or less, and the symbol * indicates that each p value with respect to the value of the control group is 0.001 or less, respectively. Further, the amount of PCSK9 in the blood are shown in FIG. 5. In the figure, FIG. 5A indicates the amount of PCSK9 in the blood of male mice, and FIG. 5B indicates the amount of PCSK9 in the blood of female mice, respectively. The symbol * indicates that each p value with respect to the value of the control group is 0.05 or less, the symbol  indicates that each p value with respect to the value of the control group is 0.01 or less, and the symbol * indicates that each p value with respect to the value of the control group is 0.001 or less, respectively.

As shown in FIG. 4, administration of PRD125 markedly reduced the amount of triglyceride in the liver and the blood. Further, as shown in FIG. 5, administration of PRD125 also significantly reduced the amount of PCSK9 in the blood.

The present disclosure is not limited to the aforementioned examples and includes various modifications. For example, the aforementioned examples have been described in detail in order to explain the present disclosure in an easy-to-understand manner, and are not necessarily limited to those having all the described configurations. In addition, it is possible to add, delete, and/or replace a part of the configuration of each embodiment with another configuration.

All publications, patents, and patent applications cited herein are incorporated herein by reference in their entirety.

The invention claimed is:

1. An in vivo method of inhibiting pro-protein convertase subtilisin/kexin type 9 (PCSK9) in a mammal, the method comprising administering to the mammal an effective amount of a compound selected from the group consisting of 1,11-O-o-methylbenzylidene-7-O-p-cyanobenzoyl-1,7,11-trideacetyl pyripyropene A (PRD125), 7-p-cyanobenzoyl-7-deacetyl pyripyropene A (PRD017), and 7-O-p-cyanobenzoyl-1,11-di(O-isobutyryl)-1,7,11-trideacetyl pyripyropene A (PRD056), or a pharmaceutically-acceptable salt or solvate thereof, as an active component.

2. The method of claim 1, further comprising co-administering a statin or ezetimibe.

3. The method of claim 1 or claim 2, wherein the compound is PRD125.

4. The method of claim 1 or claim 2, wherein the compound is PRD017.

5. The method of claim 1 or claim 2, wherein the compound is PRD056.

* * * * *